United States Patent
Iizuka et al.

(10) Patent No.: US 7,971,630 B2
(45) Date of Patent: Jul. 5, 2011

(54) METHOD AND APPARATUS FOR DETECTING A CRATER END OF A CONTINUOUSLY CAST PRODUCT

(75) Inventors: Yukinori Iizuka, Kanagawa (JP); Jun Kubota, Okayama (JP); Koichi Tsutsumi, Chiba (JP)

(73) Assignee: JFE Steel Corporation, Tokyo (JP)

( * ) Notice: Subject to any disclaimer, the term of this patent is extended or adjusted under 35 U.S.C. 154(b) by 0 days.

(21) Appl. No.: 12/657,692

(22) Filed: Jan. 26, 2010

(65) Prior Publication Data
US 2010/0163206 A1    Jul. 1, 2010

Related U.S. Application Data

(62) Division of application No. 10/579,943, filed as application No. PCT/JP2004/017824 on Nov. 24, 2004, now Pat. No. 7,740,051.

(30) Foreign Application Priority Data

Nov. 27, 2003 (JP) ................................. 2003-396827

(51) Int. Cl.
B22D 11/00 (2006.01)
B22D 11/16 (2006.01)
(52) U.S. Cl. ...................... 164/451; 164/151.2; 164/452
(58) Field of Classification Search .................. 164/451, 164/452, 454, 455, 413, 414, 151.2, 154.2
See application file for complete search history.

(56) References Cited

U.S. PATENT DOCUMENTS

| | | | |
|---|---|---|---|
| 6,896,035 B2 | 5/2005 | Iizuka et al. | |
| 7,740,051 B2 * | 6/2010 | Iizuka et al. | 164/451 |
| 2003/0141036 A1 | 7/2003 | Iizuka et al. | |

FOREIGN PATENT DOCUMENTS

| | | |
|---|---|---|
| EP | 1 298 429 A1 | 4/2003 |
| JP | 55-158506 A | 12/1980 |
| JP | 57-032863 A | 2/1982 |
| JP | 62-148850 | * 7/1987 |
| JP | 62-148850 A | 7/1987 |

(Continued)

OTHER PUBLICATIONS

Aug. 11, 2009 Office Action in Japanese application 2004-327638 (along with an English-language translation thereof).

(Continued)

*Primary Examiner* — Kevin P Kerns
(74) *Attorney, Agent, or Firm* — Holtz, Holtz, Goodman & Chick, P.C.

(57) ABSTRACT

A method for detecting a crater end of a continuously cast product, including installing an ultrasonic shear wave sensor for transmitting an ultrasonic shear wave to the continuously cast product and receiving the transmitted ultrasonic shear wave in a continuous casting machine, detecting based on variations of an ultrasonic signal received by the ultrasonic shear wave sensor that the crater end of the cast product is matched with the installed position of the ultrasonic shear wave sensor, calibrating a physical property value used in a calculation based on a heat condition equation such that the crater end computed based on the heat condition equation using casting conditions at that time is matched with the installed position of the ultrasonic shear wave sensor, and after the calibration, determining the crater end by the calculation based on the heat condition equation under respective casting conditions by using the calibrated physical property value.

13 Claims, 8 Drawing Sheets

FOREIGN PATENT DOCUMENTS

| | | |
|---|---|---|
| JP | 63-313643 A | 12/1988 |
| JP | 01-127161 A | 5/1989 |
| JP | 02-055909 A | 2/1990 |
| JP | 05-123842 A | 5/1993 |
| JP | 2002-014083 A | 1/2002 |
| JP | 2003-103351 A | 4/2003 |
| JP | 2005-277860 A | 7/2005 |

OTHER PUBLICATIONS

Dec. 8, 2009 Office Action in Japanese application 2004-327638.
European Search Report dated Jan. 21, 2010 in EP 09 01 3900.

* cited by examiner

METHOD AND APPARATUS FOR DETECTING A CRATER END OF A CONTINUOUSLY CAST PRODUCT

CROSS-REFERENCE TO RELATED APPLICATIONS

This application is a divisional application of application Ser. No. 10/579,943 filed May 22, 2006 (U.S. Pat. No. 7,740, 051), which is the United States national phase application of International application PCT/JP2004/017824 filed Nov. 24, 2004. The entire contents of each of application Ser. No. 10/579,943 and PCT/JP2004/017824 are hereby incorporated by reference herein.

TECHNICAL FIELD

The present invention relates to a method and apparatus for detecting a crater end of a continuously cast product online, which is under a casting process in a continuous casting machine, and also relates to a method for producing a continuously cast product.

BACKGROUND ART

In continuous casting of steel, it is very important to determine at which position in a continuously cast product is completed solidification of the continuously cast product (hereinafter referred to as a "crater end"). The reason is that detection of the crater end contributes to greatly improving productivity and quality of the cast product.

For example, when the casting speed is increased to improve productivity, the crater end is moved downstream in the casting direction of the cast product. If the crater end exceeds the range of rolls supporting the cast product, the cast product is bulged by the action of static iron pressure (hereinafter referred to as "bulging") and internal quality is deteriorated. In the event of giant bulging, shutdown of the casting process may be caused. Accordingly, if the crater end is not definitely confirmed, the casting speed cannot be increased beyond a conservatively set level.

Also, in soft reduction operation aiming to reduce central segregation in a cast product and to achieve higher quality, the casting speed and the intensity of secondary cooling water have to be controlled so that the crater end is positioned within a soft reduction zone. Further, in the case of a slab having a compressed shape, it is known that the crater end is not uniform in the transverse direction of the slab and the shape of the crater end is varied with time. Such a variation in the shape of the crater end is also a major factor deciding the quality and productivity of the slab.

Because of the necessity of determining solidification of a cast product (hereinafter referred to also as a "slab") in order to meet the above-mentioned requirements, various methods for determining solidification of the slab have been proposed so far.

A currently generally practiced method comprises the steps of performing calculation based on the heat condition equation in solidifying a slab and estimating, as the crater end, a position where the temperature in a central portion of the slab represents the solidus (see, e.g., Patent Document 1).

A method for directly measuring the crater end online is also tried. For example, Patent Document 2 discloses a method comprising the steps of propagating an ultrasonic longitudinal wave through a slab by using a transmitter and a receiver for electromagnetic ultrasonic, and determining respective thicknesses of a solid phase and a liquid phase from the following formula (1) based on the propagation time of an ultrasonic longitudinal wave signal passing through a slab, the thickness of the slab, and the previously-measured ultrasonic velocities of the longitudinal wave in the solid phase and the liquid phase. In the formula (1), d is the thickness of the solid phase, t is the propagation time, D is the thickness of the slab, $V_l$ is the average ultrasonic velocity of the longitudinal wave in the liquid phase, and $V_S$ is the average ultrasonic velocity of the longitudinal wave in the solid phase.

$$d = \frac{\left(t - \frac{D}{V_l}\right)}{2 \times \left(\frac{1}{V_s} - \frac{1}{V_l}\right)} \Lambda \quad (1)$$

Patent Document 3 discloses a method for estimating the crater end based on the correlation among the thickness of the solid phase (=thickness of a solidified shell) determined as described above, the distance in the lengthwise direction of the casting process, and the amount of change in the thickness of the solid phase. Further, Patent Document 4 discloses a method comprising the steps of, in consideration of temperature dependency of the ultrasonic velocity of the longitudinal wave in the solid phase, calculating an average value of the ultrasonic velocity from a temperature distribution of the solid phase, and determining the thickness of the solid phase with high accuracy by using that average value.

In addition, there is proposed a method comprising the steps of propagating an ultrasonic shear wave through a slab by using a transmitter and a receiver for electromagnetic ultrasonic, and determining whether the crater end has reached the position where the transmitter and the receiver for electromagnetic ultrasonic are installed, by utilizing such a property that the shear wave does not propagate through the liquid phase (see, e.g., Patent Documents 5 and 6).

Patent Document 1: Japanese Unexamined Patent Application Publication No. 5-123842
Patent Document 2: Japanese Unexamined Patent Application Publication No. 55-158506
Patent Document 3: Japanese Unexamined Patent Application Publication No. 57-32863
Patent Document 4: Japanese Unexamined Patent Application Publication No. 2-55909
Patent Document 5: Japanese Unexamined Patent Application Publication No. 63-313643
Patent Document 6: Japanese Unexamined Patent Application Publication No. 2002-14083

DISCLOSURE OF THE INVENTION

However, those known methods have problems as follows.
As to the method employing the calculation based on the heat condition equation, values of physical properties used in the calculation differ depending on chemical components, but all those values of physical properties are not known in all temperature ranges. This means the necessity of adaptation of the values of physical properties. Therefore, the values of physical properties have to be adapted when used in the calculation based on the heat condition equation by, e.g., a rivet method. More specifically, a metal-made rivet is driven into a slab under the casting, and a driven portion of the rivet is cut and polished after cooling to measure how far the rivet has been melted, thereby confirming the thickness of the solid phase. Then, the adaptation of the heat condition equation is made in comparison with the measurement result. Those operations are very troublesome and require a high cost. Further, it is practically impossible to perform the rivet method for all varieties of chemical components. For that reason, the method employing the heat condition equation has the problem that an application range is limited and high accuracy cannot be obtained.

With the method using the ultrasonic longitudinal wave, the thickness of the solid phase is calculated from the ultrasonic velocities of the longitudinal wave in the solid phase and the liquid phase, but those ultrasonic velocities differ depending on chemical components. Because those ultrasonic velocities are also not known for all varieties of chemical components, the slab rivet method, for example, is required to calibrate the measured value obtained from the propagation time. Accordingly, it is practically impossible to perform the calibration for all varieties of chemical components as with the above method employing the heat condition equation. Further, the thickness of the slab requires to be known when the thickness of the solid phase is calculated. However, because the slab containing a liquid core undergoes bulging, it is also difficult to stably measure the thickness of the slab under casting, thus deteriorating the measurement accuracy.

With the method using the ultrasonic shear wave, it is usually just determined whether the crater end has reached the position where the transmitter and the receiver for electromagnetic ultrasonic are installed, by utilizing such a property that the ultrasonic shear wave does not propagate through the liquid phase. Therefore, the crater end cannot be detected by installing only one pair of the transmitter and the receiver, and many pairs of the transmitter and the receiver must be installed in the casting direction to detect the crater end. Also, Patent Documents 5 and 6 state that the crater end upstream of the installed position of the transmitter and the receiver can be estimated from the propagation time of an ultrasonic shear wave signal which is passed through the slab. However, when the crater end is positioned downstream of the installed position of the transmitter and the receiver, an ultrasonic passage signal cannot be obtained by the method using the ultrasonic shear wave, and hence the crater end cannot be detected.

The present invention has been made with the view of solving the problems mentioned above, and its object is to provide a method and apparatus for detecting a crater end of a continuously cast product, which can accurately detect the crater end only from a value measured by a sensor without needing calibration based on the slab rivet method, and further to provide a method for producing a continuously cast product, which can improve productivity or quality by utilizing information of the crater end obtained from the method and apparatus for detecting the crater end.

The inventors have conducted intensive studies and researches aiming to achieve the above object. The results of the studies and researches are as follows.

As a result of repeatedly simulating the propagation time with respect to the method for estimating the thickness of a solid phase from the propagation time of the ultrasonic longitudinal wave signal in the continuously cast product (slab), the inventors have found that dependency of the ultrasonic velocity of the longitudinal wave upon chemical components and an influence of the slab thickness are large, and accurate measurement cannot be performed based on the above-mentioned formula (1) without calibration. On the other hand, the inventors also have found that, when the crater end is positioned downstream of an ultrasonic longitudinal wave sensor in the casting direction and a liquid phase is contained in a propagation path of the ultrasonic wave, the propagation time measured by the ultrasonic longitudinal wave sensor is changed depending on the thickness of the solid phase with good sensitivity because the ultrasonic velocity in the liquid phase is slower than that in the solid phase, whereby very high accuracy is obtained in the measured value of the thickness of the solid phase and in relative measurement of the crater end derived from the thickness of the solid phase.

Similarly, as a result of studying the method of determining the crater end based on the heat condition equation, the inventors have found that, in trying to determine the crater end with high accuracy under various casting conditions and varieties of chemical components, the crater end cannot be accurately determined without calibrating the values of physical properties used in the calculation.

As a method for calibrating online the values of physical properties used in estimating the thickness of the solid phase from the propagation time of the ultrasonic longitudinal wave signal and the values of physical properties used in the calculation based on the heat condition equation, the inventors have reviewed a process of performing calibration by utilizing the crater end determined based on such a property that the ultrasonic shear wave does not propagate through the liquid phase. The review has been made with a test of using an ingot having a liquid core, radiating the ultrasonic shear wave to pass through the ingot while cooling it, and measuring the temperature of a core portion of the ingot at the same time. From the test result, it has been confirmed that, the timing at which the ultrasonic shear wave does no longer propagate through the ingot corresponds to the timing at which a solid phase rate of the ingot core becomes 1, i.e., the timing at which solidification is completed (core temperature=solidus), without depending on the chemical components. Thus, the inventors have gained the finding that, based on such a property, absolute value measurement can be performed on the crater end which is matched with the installed position of an ultrasonic shear wave sensor at the timing at which a passage signal from the ultrasonic shear wave sensor disappears from a detected state, or the timing at which the passage signal from the ultrasonic shear wave sensor appears from an undetected state, regardless of the chemical components and the casting conditions.

According to that finding, the method for estimating the crater end by using the ultrasonic longitudinal wave and the method for estimating the crater end based on the heat condition equation, which are superior in accuracy of relative measurement, can be used as a detection means, which is also superior in absolute measurement, by calibrating a calculation formula for computing the crater end, such as the above-mentioned formula (1), or calibrating the values of physical properties used in the calculations based on the heat condition equation on condition that the crater end is matched with the installed position of the ultrasonic shear wave sensor. As another finding confirmed, such a detection method can overcome the problem that, in the case of using only the ultrasonic shear wave, the crater end cannot be measured under the casting conditions where the crater end is positioned downstream of the ultrasonic shear wave sensor in the casting direction.

In practice, the calculation formula for determining the crater end from the propagation time can be calibrated by deciding the values of physical properties so that the crater end computed from the propagation time measured by the ultrasonic longitudinal wave sensor is matched with the installed position of the ultrasonic shear wave sensor. Similarly, the heat condition equation can be calibrated by performing the calculation based on the heat condition equation under the casting conditions that the crater end is matched with the installed position of an ultrasonic shear wave sensor, and deciding the values of physical properties so that the crater end determined by the calculation based on the heat condition equation is matched with the installed position of the ultrasonic shear wave sensor. Thereafter, by employing the calibrated calculation formula for determining the crater end from the propagation time or the calibrated heat condition equation, it is possible to determine the crater end with high accuracy when the casting conditions are changed, for example, when the casting speed is further increased.

In this connection, the inventors have gained the finding as follows. When the crater end is estimated from the propagation time measured by the ultrasonic longitudinal wave sensor, the accuracy in measurement of the crater end can be greatly improved by installing a second ultrasonic shear wave sensor downstream of the ultrasonic shear wave sensor, which provides a first calibration point, in the casting direction, and calibrating the calculation formula for computing the crater end, such as the above-mentioned formula (1), under the casting conditions where the installed position of the second ultrasonic shear wave sensor is matched with the crater end.

Still another finding is as follows. When the crater end is positioned downstream of the ultrasonic longitudinal wave sensor in the casting direction and the liquid phase is contained in the propagation path of the ultrasonic longitudinal wave, the propagation time is changed with high sensitivity depending on the thickness of the solid phase because the ultrasonic velocity in the liquid phase is much slower than that in the solid phase. On other hand, when the crater end is positioned upstream of the ultrasonic longitudinal wave sensor in the casting direction and the liquid phase is not contained in the propagation path of the ultrasonic longitudinal wave, the propagation time is not so sensitivity changed even when the casting conditions are changed. In order to improve the accuracy in measurement of the crater end, therefore, different calculation formulae are preferably used as the calculation formula for computing the crater end between when the crater end is upstream of the installed position of the ultrasonic longitudinal wave sensor and when the crater end is downstream of the same.

Further, from the viewpoint of installing both the ultrasonic shear wave sensor and the ultrasonic longitudinal wave sensor in a narrow gap between two adjacent rolls supporting the slab, the ultrasonic shear wave sensor and the ultrasonic longitudinal wave sensor are preferably constituted as an integral unit. As a result of studying how to realize the integral unit of the ultrasonic shear wave sensor and the ultrasonic longitudinal wave sensor, it has been confirmed that the ultrasonic shear wave sensor and the ultrasonic longitudinal wave sensor can be constituted as the integral unit by forming an integral sensor having three or more magnetic poles in the transverse direction of the slab and made up of a longitudinal wave coil arranged so as to wind the surrounding of an inner magnetic pole aside from its surface and a shear wave coil arranged so as to overlie the magnetic pole surface.

On the other hand, in relation to the case of determining the crater end based on the heat condition equation, the inventors have gained the finding given below. The crater end can be detected from the measured value of the propagation time through the steps of installing a propagation time measuring sensor, which is the same as the above-mentioned ultrasonic shear wave sensor or a separate sensor for measuring the propagation time of the ultrasonic longitudinal or shear wave signal, to thereby obtain the measured values of the propagation time under various casting conditions, determining the crater ends based on the calibrated heat condition equation at the same time, preparing a relation formula or a table representing the relationship between the determined crater ends and the measured values of the propagation time, and determining the crater end from the measured value of the propagation time by utilizing the prepared relation formula or table with no need of performing the calculation based on the heat condition equation for each measurement.

The present invention has been made based on, the above-described results of the studies. According to a first aspect, the present invention provides a method for detecting a crater end of a continuously cast product, the method comprising the steps of installing an ultrasonic shear wave sensor for transmitting an ultrasonic shear wave to the continuously cast product and receiving the transmitted ultrasonic shear wave and an ultrasonic longitudinal wave sensor for transmitting an ultrasonic longitudinal wave to the continuously cast product and receiving the transmitted ultrasonic longitudinal wave at the same position in a continuous casting machine or at two positions apart, from each other in a casting direction but at the same position in a transverse direction of the cast product, detecting based on variations of an ultrasonic signal received by the ultrasonic shear wave sensor that the crater end of the cast product is matched with the installed position of the ultrasonic shear wave sensor, calibrating a calculation formula for determining the crater end from a propagation time of an ultrasonic longitudinal wave signal such that the crater end computed from the propagation time of the ultrasonic longitudinal wave signal at that time is matched with the installed position of the ultrasonic shear wave sensor, and after the calibration, determining the crater end from the propagation time of the ultrasonic longitudinal wave signal based on the calibrated calculation formula.

According to a second aspect of the present invention, in the method for detecting a crater end of a continuously cast product according to the first aspect, the method further comprising the steps of installing a second ultrasonic shear wave sensor downstream of the ultrasonic shear wave sensor in the casting direction at the same position in the transverse direction of the cast product, detecting based on variations of an ultrasonic signal received by the second ultrasonic shear wave sensor that the crater end of the cast product is matched with the installed position of the second ultrasonic shear wave sensor, and further calibrating the calculation formula for determining the crater end from the propagation time of the ultrasonic longitudinal wave signal such that the crater end computed from the propagation time of the ultrasonic longitudinal wave signal at that time is matched with the installed position of the second ultrasonic shear wave sensor.

According to a third aspect of the present invention, in the method for detecting a crater end of a continuously cast product according to the first or second aspect, the calculation formula for determining the crater end from the propagation time of the ultrasonic longitudinal wave signal differs between when the crater end is positioned upstream of the installed position of the ultrasonic longitudinal wave sensor in the casting direction and when the crater end is positioned downstream thereof.

According to a fourth aspect, the present invention provides a method for detecting a crater end of a continuously cast product, the method comprising the steps of installing an ultrasonic shear wave sensor for transmitting an ultrasonic shear wave to the continuously cast product and receiving the transmitted ultrasonic shear wave in a continuous casting machine, detecting based on variations of an ultrasonic signal received by the ultrasonic shear wave sensor that the crater end of the cast product is matched with the installed position of the ultrasonic shear wave sensor, calibrating a physical property value used in calculation based on a heat condition equation such that the crater end computed based on the heat condition equation using casting conditions at that time is matched with the installed position of the ultrasonic shear wave sensor, and after the calibration, determining the crater end by the calculation based on the heat condition equation under respective casting conditions by using the calibrated physical property value.

According to a fifth aspect, the present invention provides a method for detecting a crater end of a continuously cast product, the method comprising the steps of installing an ultrasonic shear wave sensor for transmitting an ultrasonic shear wave to the continuously cast product and receiving the transmitted ultrasonic shear wave in a continuous casting machine, detecting based on variations of an ultrasonic signal received by the ultrasonic shear wave sensor that the crater end of the cast product is matched with the installed position of the ultrasonic shear wave sensor, calibrating a physical property value used in calculation based on a heat condition equation such that the crater end computed based on the heat condition equation using casting conditions at that time is matched with the installed position of the ultrasonic shear wave sensor, determining the crater ends by the calculation based on the heat condition equation by using the calibrated physical property value and measuring the propagation times by the ultrasonic shear wave sensor under various casting conditions, obtaining a relationship between the crater ends computed based on the heat condition equation and the propagation times measured by the ultrasonic shear wave sensor, and determining the crater end from the propagation time measured by the ultrasonic shear wave sensor based on the obtained relationship.

According to a sixth aspect, the present invention provides a method for detecting a crater end of a continuously cast product, the method comprising the steps of installing, in a continuous casting machine, a first ultrasonic shear wave sensor for transmitting an ultrasonic shear wave to the continuously cast product and receiving the transmitted ultrasonic shear wave and at least one of an ultrasonic longitudinal wave sensor for transmitting an ultrasonic longitudinal wave to the continuously cast product and receiving the transmitted ultrasonic longitudinal wave and a second ultrasonic shear wave sensor for transmitting an ultrasonic shear wave and receiving the transmitted ultrasonic shear wave, detecting based on variations of an ultrasonic signal received by the first ultrasonic shear wave sensor that the crater end of the cast product is matched with the installed position of the first ultrasonic shear wave sensor, calibrating a physical property value used in calculation based on a heat condition equation such that the crater end computed based on the heat condition equation using casting conditions at that time is matched with the installed position of the first ultrasonic shear wave sensor, determining the crater ends by the calculation based on the heat condition equation by using the calibrated physical property value and measuring the propagation times by the ultrasonic longitudinal wave sensor or the second ultrasonic shear wave sensor under various casting conditions, obtaining a relationship between the crater ends computed based on the heat condition equation and the propagation times measured by the ultrasonic longitudinal wave sensor or the second ultrasonic shear wave sensor, and determining the crater end from the propagation time measured by the ultrasonic longitudinal wave sensor or the second ultrasonic shear wave sensor based on the obtained relationship.

According to a seventh aspect, the present invention provides a method for detecting a crater end of a continuously cast product, the method comprising the step of, from a propagation time of an ultrasonic longitudinal wave signal measured by an ultrasonic longitudinal wave sensor installed in the continuous casting machine for which the calibration has been made or in a different continuous casting machine, determining the crater end in the relevant continuous casting machine by using the calculation formula calibrated by the method according to any one of the first to third aspects of the present invention.

According to an eighth aspect, the present invention provides a method for detecting a crater end of a continuously cast product, the method comprising the steps of executing the calculation based on the heat condition equation by using the physical property value calibrated by the method according to the fourth aspect of the present invention and the casting conditions of the continuous casting machine for which the calibration has been made or of a different continuous casting machine, and determining the crater end in the relevant continuous casting machine.

According to a ninth aspect, the present invention provides a method for detecting a crater end of a continuously cast product, the method comprising the step of, based on the relationship between the crater ends computed based on the heat condition equation and the propagation times measured by the ultrasonic sensor, which is obtained by the method according to the fifth or sixth aspect of the present invention, determining the crater end in a target continuous casting machine from a propagation time of an ultrasonic signal measured by an ultrasonic shear wave sensor or an ultrasonic longitudinal wave sensor installed in the continuous casting machine for which the relationship has been obtained or in a different continuous casting machine.

According to a tenth aspect, the present invention provides a method for detecting a crater end of a continuously cast product, the method comprising the steps of determining the crater end of the cast product by the method for detecting a crater end of a continuously cast product according to any one of the first to sixth aspects of the present invention, and adjusting a casting speed or intensity of secondary cooling for the cast product in accordance with the determination result.

According to an eleventh aspect, the present invention provides an apparatus for detecting a crater end of a continuously cast product, the apparatus comprising an ultrasonic shear wave sensor made up of an ultrasonic shear wave transmitter for transmitting an ultrasonic shear wave to the continuously cast product and an ultrasonic shear wave receiver for receiving the transmitted ultrasonic shear wave, an ultrasonic longitudinal wave sensor made up of an ultrasonic longitudinal wave transmitter for transmitting an ultrasonic longitudinal wave to the continuously cast product and an ultrasonic longitudinal wave receiver for receiving the transmitted ultrasonic longitudinal wave, the ultrasonic longitudinal wave sensor being installed at the same position in a continuous casting machine as the ultrasonic shear wave sensor or a position apart from the ultrasonic shear wave sensor in a casting direction but at the same position in a transverse direction of the cast product, and a crater end computing unit for determining the crater end of the cast product by using a calculation formula in accordance with an ultrasonic signal received by the ultrasonic longitudinal wave sensor, wherein at the time when it is confirmed based on variations of an ultrasonic signal received by the ultrasonic shear wave sensor that the installed position of the ultrasonic shear wave sensor and the crater end of the cast product are matched with each other, the calculation formula is calibrated such that the crater end computed based on the calculation formula is matched with the installed position of the ultrasonic shear wave sensor.

According to a twelfth aspect of the present invention, in the apparatus for detecting a crater end of a continuously cast product according to the eleventh aspect, the apparatus further comprising a second ultrasonic shear wave sensor installed downstream of the ultrasonic shear wave sensor in the casting direction at the same position in the transverse direction of the cast product, wherein at the time when it is confirmed based on variations of an ultrasonic signal received by the second ultrasonic shear wave sensor that the installed position of the second ultrasonic shear wave sensor and the crater end of the cast product are matched with each other, the calculation formula is further calibrated such that the crater end computed based on the calculation formula is matched with the installed position of the second ultrasonic shear wave sensor.

According to a thirteenth aspect of the present invention, in the apparatus for detecting a crater end of a continuously cast product according to the eleventh or twelfth aspect, the ultrasonic shear wave transmitter and the ultrasonic longitudinal wave transmitter are installed on one side of the cast product, the ultrasonic shear wave receiver and the ultrasonic longitudinal wave receiver are installed on the other side of the cast product, and a set of the ultrasonic shear wave transmitter and the ultrasonic longitudinal wave transmitter and a set of the ultrasonic shear wave receiver and the ultrasonic longitudinal wave receiver are each constituted as an integral electromagnetic ultrasonic sensor having three or more magnetic poles in the transverse direction of the cast product and made up of a longitudinal wave coil arranged to wind the surrounding of an inner magnetic pole aside from a surface thereof and a shear wave coil arranged to overlie the magnetic pole surface.

According to a fourteenth aspect, the present invention provides an apparatus for detecting a crater end of a continuously cast product, the apparatus comprising an ultrasonic shear wave sensor made up of an ultrasonic shear wave transmitter for transmitting an ultrasonic shear wave to the continuously cast product and an ultrasonic shear wave receiver for receiving the transmitted ultrasonic shear wave, and a heat condition equation unit for executing calculation based on a heat condition equation in accordance with casting conditions and values of physical properties, thereby determining the crater end of the cast product, wherein at the time when it is confirmed based on variations of an ultrasonic signal received by the ultrasonic shear wave sensor that the installed position of the ultrasonic shear wave sensor and the crater end of the cast product are matched with each other, at least one of the values of physical properties used in the calculation based on the heat condition equation is calibrated such that the crater end computed by the heat condition equation unit is matched with the installed position of the ultrasonic shear wave sensor.

According to a fifteenth aspect, the present invention provides an apparatus for detecting a crater end of a continuously cast product, the apparatus comprising an ultrasonic shear wave sensor made up of an ultrasonic shear wave transmitter for transmitting an ultrasonic shear wave to the continuously cast product and an ultrasonic shear wave receiver for receiving the transmitted ultrasonic shear wave, a heat condition equation unit for executing calculation based on a heat condition equation in accordance with casting conditions and values of physical properties, thereby determining the crater end of the cast product, and a crater end estimating unit for estimating the crater end of the cast product based on a relationship between an ultrasonic signal received by the ultrasonic shear wave sensor and the crater end computed by the heat condition equation unit, wherein at the time when it is confirmed based on variations of the ultrasonic signal received by the ultrasonic shear wave sensor that the installed position of the ultrasonic shear wave sensor and the crater end of the cast product are matched with each other, at least one of the values of physical properties used in the calculation based on the heat condition equation is calibrated such that the crater end computed by the heat condition equation unit is matched with the installed position of the ultrasonic shear wave sensor, wherein after the calibration of the physical property value, the crater end estimating unit obtains a relationship between the ultrasonic signal received by the ultrasonic shear wave sensor and the crater end computed by the heat condition equation unit, and wherein the crater end is determined from a propagation time measured by the ultrasonic shear wave sensor based on the obtained relationship.

According to a sixteenth aspect, the present invention provides an apparatus for detecting a crater end of a continuously cast product, the apparatus comprising an ultrasonic shear wave sensor made up of an ultrasonic shear wave transmitter for transmitting an ultrasonic shear wave to the continuously cast product and an ultrasonic shear wave receiver for receiving the transmitted ultrasonic shear wave, an ultrasonic longitudinal wave sensor made up of an ultrasonic longitudinal wave transmitter for transmitting an ultrasonic longitudinal wave to the continuously cast product and an ultrasonic longitudinal wave receiver for receiving the transmitted ultrasonic longitudinal wave, a heat condition equation unit for executing calculation based on a heat condition equation in accordance with casting conditions and values of physical properties, thereby determining the crater end of the cast product, and a crater end estimating unit for estimating the crater end of the cast product based on a relationship between an ultrasonic signal received by the ultrasonic shear wave sensor and the crater end computed by the heat condition equation unit, wherein at the time when it is confirmed based on variations of the ultrasonic signal received by the ultrasonic shear wave sensor that the installed position of the ultrasonic shear wave sensor and the crater end of the cast product are matched with each other, at least one of the values of physical properties used in the calculation based on the heat condition equation is calibrated such that the crater end computed by the heat condition equation unit is matched with the installed position of the ultrasonic shear wave sensor, wherein after the calibration of the physical property value, the crater end estimating unit obtains a relationship between an ultrasonic signal received by the ultrasonic longitudinal wave sensor and the crater end computed by the heat condition equation unit, and wherein the crater end is determined from a propagation time measured by the ultrasonic longitudinal wave sensor based on the obtained relationship.

The term "the same position in the transverse direction of the cast product" used in the present invention means a range within which change of the crater end in the casting direction is substantially negligible. The crater end sometimes differs in the transverse direction of the cast product in the slab continuous casting machine. In the case of directly determining the crater end from the propagation time of the ultrasonic longitudinal wave signal without executing the calculation based on the heat condition equation, therefore, the ultrasonic shear wave sensor and the ultrasonic longitudinal wave sensor have to be disposed so as to detect the same crater end or to be positioned within such a range in the transverse direction that, even if the crater end is changed in the casting direction, a relative change in positions of the crater end, which are detected by the ultrasonic shear wave sensor and the ultrasonic longitudinal wave sensor, can be regarded substantially not present. More specifically, when the shape of the crater end in the transverse direction of the cast product can be regarded flat, the ultrasonic shear wave sensor and the ultrasonic longitudinal wave sensor may be apart from each other by a distance of several 100's mm. Conversely, when the shape of the crater end in the transverse direction of the cast product is changed to a large extent, the distance between those two sensors has to be kept within several 10's mm. The reason is as follows. The ultrasonic wave used in the intended purpose has a wavelength of several 10's mm, and the sensor size is also several 10's mm. Taking into account the influence of diffraction as well, therefore, positions within several 10's mm can be regarded as the same position. Also, the term "the same position in a continuous casting machine" means the same position not only in the transverse direction of the cast product, but also in the casting direction. The term "the same position in the casting direction" means that the sensors are installed in the same gap between the cast-product support rolls.

BEST MODE FOR CARRYING OUT THE INVENTION

Figure 1:
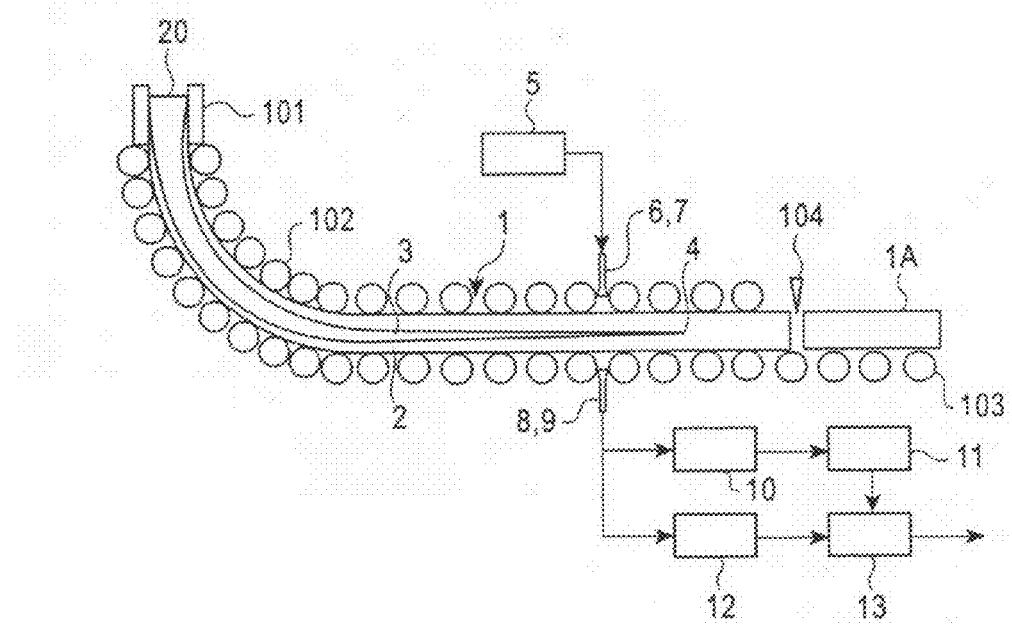
FIG. 1 shows a first embodiment of the present invention.

The present invention will be described in detail below with reference to the accompanying drawings. A method and apparatus for directly detecting a crater end from the propagation time of an ultrasonic longitudinal wave signal measured by an ultrasonic longitudinal wave sensor will be first described. FIG. 1 shows a first embodiment of the present invention related to the method and apparatus for directly detecting the crater end from the propagation time of the ultrasonic longitudinal wave signal measured by the ultrasonic longitudinal wave sensor. In other words, FIG. 1 is a schematic view of a slab continuous casting machine provided with a crater end detector according to the present invention, in which an ultrasonic shear wave sensor and the ultrasonic longitudinal wave sensor are installed at the same position in the continuous casting machine.

In FIG. 1, reference numeral 1 denotes a cast product (slab), 2 denotes a solid phase, 3 denotes a liquid phase, and 4 denotes a crater end. Molten steel poured into a mold 101 of the continuous casting machine is cooled by the mold 101 to form the solidified portion 2. The slab 1 having the inner liquid phase 3 in a not-solidified state and the solidified portion 2 surrounding the inner liquid phase 3 is withdrawn downward of the mold 101 while being supported by plural pairs of slab support rolls 102 which are disposed successively under the mold 101 in opposed relation. Secondary cooling zones (not shown) made up of air mist spray nozzles, water spray nozzles, etc. and spraying cooling water toward surfaces of the slab 1 are installed in gaps between the slab support rolls 102 adjacent to each other in the casting direction. The slab 1 is cooled by the secondary cooling zones while being withdrawn downward in the casting direction, and is then completely solidified up to its core. A position where the slab is completely solidified up to the core is the crater end 4. The completely solidified slab 1 is cut into a predetermined length by a slab cutting machine 104 installed downstream of the slab support rolls 102 and is conveyed out of the casting site as a cut slab 1A by conveying rolls 103.

The crater end detector according to the present invention is installed in the slab continuous casting machine constructed as described above. The crater end detector according to the present invention comprises an ultrasonic shear wave sensor made up of an ultrasonic shear wave transmitter 6 and an ultrasonic shear wave receiver 8 disposed in opposed relation with the slab 1 between them, an ultrasonic longitudinal wave sensor made up of an ultrasonic longitudinal wave transmitter 7 and an ultrasonic longitudinal wave receiver 9 disposed in opposed relation with the slab 1 between them, and an ultrasonic transmitting unit 5 which is an electric circuit for supplying an electric signal to each of the ultrasonic shear wave transmitter 6 and the ultrasonic longitudinal wave transmitter 7, thereby causing ultrasonic waves to be transmitted to the slab 1. The crater end detector further comprises a passed shear-wave intensity detecting unit 10, a crater end arrival detecting unit 11, a longitudinal-wave propagation time detecting unit 12, and a crater end computing unit 13 for processing signals received by the ultrasonic shear wave receiver 8 and the ultrasonic longitudinal wave receiver 9. The ultrasonic waves transmitted from the ultrasonic shear wave transmitter 6 and the ultrasonic longitudinal wave transmitter 7 pass through the slab 1 and are received by the ultrasonic shear wave receiver 8 and the ultrasonic longitudinal wave receiver 9, respectively, for conversion to electric signals.

The passed shear-wave intensity detecting unit 10 detects the intensity of the ultrasonic shear wave signal received by the ultrasonic shear wave receiver 8. The crater end arrival detecting unit 11 determines whether the crater end 4 is positioned upstream or downstream of the installed position of the ultrasonic shear wave transmitter 6 and the ultrasonic shear wave receiver 8 in the casting direction, based on variations of an ultrasonic shear wave passage signal detected by the passed shear-wave intensity detecting unit 10. The longitudinal-wave propagation time detecting unit 12 detects the propagation time of the ultrasonic longitudinal wave signal, which is passed through the slab 1, from the signal received by the ultrasonic longitudinal wave receiver 9. The crater end computing unit 13 determines the crater end 4 with a computing process based on the propagation time of the ultrasonic longitudinal wave signal detected by the longitudinal-wave propagation time detecting unit 12. The processing in the passed shear-wave intensity detecting unit 10, the crater end arrival detecting unit 11, the longitudinal-wave propagation time detecting unit 12, and the crater end computing unit 13 is executed by a computer. Though not shown, an ultrasonic signal amplifier, an A/D converter for taking a signal waveform into the computer, etc. are required between each of the ultrasonic shear wave receiver 8 and the ultrasonic longitudinal wave receiver 9 and the computer. Additionally, in the crater end detector shown in FIG. 1, the ultrasonic shear wave transmitter 6 and the ultrasonic longitudinal wave transmitter 7 are constituted as an integral unit. Similarly, the ultrasonic shear wave receiver 8 and the ultrasonic longitudinal wave receiver 9 are also constituted as an integral unit.

Figure 2:
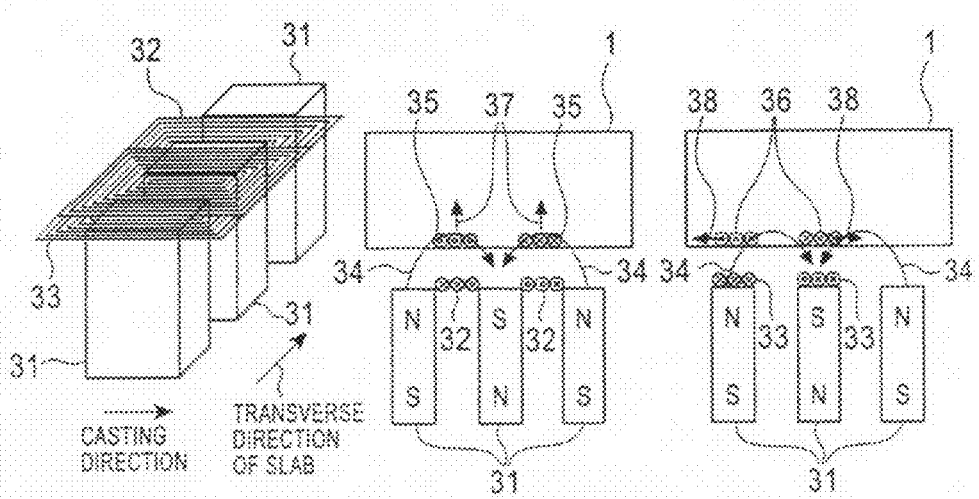
FIG. 2 shows the construction and operation of an electromagnetic ultrasonic sensor for generating and detecting an ultrasonic longitudinal wave and an ultrasonic shear wave at the same position.

An example of the integral unit of the ultrasonic shear wave transmitter 6 and the ultrasonic longitudinal wave transmitter 7 or the integral unit of the ultrasonic shear wave receiver 8 and the ultrasonic longitudinal wave receiver 9 will be described below with reference to FIG. 2. FIG. 2 is an illustration for explaining the construction and operation of an electromagnetic ultrasonic sensor for generating and detecting the ultrasonic longitudinal wave and the ultrasonic shear wave at the same position.

In FIG. 2, reference numeral 31 denotes a magnet. The magnet 31 may be any of a permanent magnet and an electromagnet, but it is preferably a permanent magnet for the reason that the electromagnetic ultrasonic sensor can be constituted in smaller size. Reference numeral 32 denotes a longitudinal wave coil which is a pancake coil arranged so as to wind the surrounding of a center magnetic pole aside from its surface. On the other hand, reference numeral 33 denotes a shear wave coil which is a pancake coil arranged so as to overlie the magnetic pole surface. Reference numeral 34 denotes a magnetic line of force generated from the magnet 31. Reference numerals 35 and 36 denote eddy currents generated in the slab 1 by the longitudinal wave coil 32 and the shear wave coil 33, respectively. The eddy currents 35 and 36 are generated upon high frequency currents supplied to the longitudinal wave coil 32 and the shear wave coil 33 from the ultrasonic transmitting unit 5.

The eddy currents 35 and 36 generated in the slab 1 cause the Lorentz's forces between the currents and static magnetic fields induced from the magnets 31 as indicated by the magnetic lines 34 of force, thereby producing an ultrasonic longitudinal wave 37 and an ultrasonic shear wave 38. Those ultrasonic waves are received through the action reversal to that in the transmission. Specifically, the slab 1 in the static magnetic field is vibrated by the ultrasonic waves to generate eddy currents in the slab 1, and the generated eddy currents are detected by the longitudinal wave coil 32 and the shear wave coil 33. Thus, the ultrasonic waves can be received using exactly the same construction as that for transmitting the ultrasonic waves.

In order to generate and detect the ultrasonic longitudinal wave and the ultrasonic shear wave at the same position in the gap between the slab support rolls adjacent to each other in the continuous casting machine, a small-sized electromagnetic ultrasonic sensor is required which can be inserted in the roll-to-roll small gap (generally 40 to 75 mm). Although the electromagnetic ultrasonic sensor is itself well known, a small-sized electromagnetic ultrasonic sensor adaptable for such a requirement, i.e., capable of generating and detecting the ultrasonic longitudinal wave and the ultrasonic shear wave at the same position, has not been proposed in the past. According to the present invention, as shown in FIG. 2, since the magnets 31 are arranged in the transverse direction of the slab 1, three or more magnetic poles can be disposed side by side. It is therefore possible to insert the electromagnetic ultrasonic sensor in the narrow gap between the slab support rolls 102 so that the ultrasonic longitudinal wave and the ultrasonic shear wave can be generated and detected at the same position. Further, because the number of sensors to be installed is reduced, not only the installation cost, but also the maintenance cost can be cut.

Practically, the electromagnetic ultrasonic sensor is preferably dimensioned such that the pole area is in the range of about 10 mm×10 mm to 30 mm×30 mm, the pole-to-pole interval is in the range of about 5 mm to 30 mm, and a horizontal magnetic field between the poles has a magnetic force of not smaller than 0.1 T. When a permanent magnet is used as the magnet 31, a rare earth-made magnet is preferable and the magnet height is about 20 mm-100 mm. The number of turns in each coil is preferably in the range of about 10 to 100. A portion of the coil projecting out of the magnetic pole in the casting direction can be bent to narrow the sensor width in the casting direction. However, if the coil is bent at a point just close the pole edge, this impedes effective utilization of the horizontal magnetic field in the casting direction, and sensitivity is deteriorated. For that reason, the coil is preferably bent at a point projected about 5 mm from the pole edge. If the projection width is about 3 mm, the effect of avoiding the deterioration of sensitivity is not sufficient. Conversely, if the projection width exceeds 10 mm, the sensor width in the casting direction is not satisfactorily reduced. Thus, the projection width in the range of about 3 mm to 10 mm is preferable.

When the above-described electromagnetic ultrasonic sensor is practically used, specifications required for an electric circuit to generate and detect the ultrasonic waves are as follows. The voltage of the transmitted signal is not lower than about 1 kV (with a current of not lower than 20 A), and the gain of a receiving amplifier is not smaller than 60 dB to 80 dB. The frequency of the transmitted signal is in the range of about 50 kHz to 150 kHz for the ultrasonic shear wave and in the range of about 100 kHz to 400 kHz for the ultrasonic longitudinal wave. The waveform of the transmitted signal can be given as any desired type of modulated signal, such as a tone burst wave obtained by generating a sine wave for a short time or a chirp wave having the amplitude and phase changed in a predetermined time span.

When the ultrasonic shear wave sensor and the ultrasonic longitudinal wave sensor are installed at the same position in the continuous casting machine, it is not always required to employ the integral electromagnetic ultrasonic sensor for generating and detecting the ultrasonic longitudinal wave and the ultrasonic shear wave at the same position. The ultrasonic shear wave sensor and the ultrasonic longitudinal wave sensor may be separately installed if the spacing between the installed positions of the ultrasonic shear wave sensor and the ultrasonic longitudinal wave sensor is within the range in which a resulting change of the crater end 4 in the casting direction can be regarded substantially not present, more specifically, within several 10's mm.

A manner for processing the received signal will be described below. First, the operation of the passed shear-wave intensity detecting unit 10 will be described with reference to FIG. 3.

Figure 3:
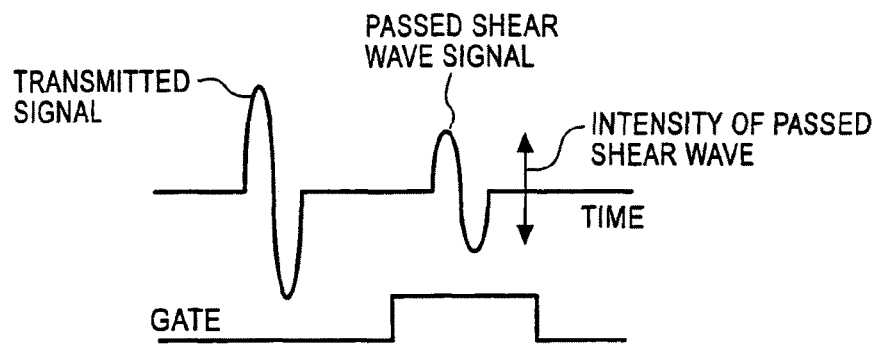
FIG. 3 shows the operation of a passed shear-wave intensity detecting unit.

FIG. 3 shows the operation of the passed shear-wave intensity detecting unit 10, and it illustrates the waveform of the received signal corresponding to one shot of the transmitted signal. In FIG. 3, a first wave is generated upon the transmitted signal electrically leaking into the ultrasonic shear wave receiver 8, and a second wave represents the ultrasonic shear wave passage signal. Because a position on the time base where the ultrasonic shear wave passage signal appears is roughly known from the thickness of the slab 1, the approximate temperature of the slab 1, and the ultrasonic velocity of the shear wave, gate for taking out the signal only at that position is provided to determine a maximum value of the signal within the gate. Such processing can be easily realized with a computing process by taking the waveform of the received signal into the computer after A/D conversion. The maximum value of the signal can be determined as an absolute value on the basis of 0 V or as a peak-to-peak value. In practice, since the transmitted signal is repeated at a cycle of several 10's Hz to several 100's Hz, it is effective, from the viewpoint of reducing influences of fluctuations due to noises, to determine the intensity of the passed ultrasonic shear wave after averaging each waveform, or to average the intensity of the passed ultrasonic shear wave for each waveform.

Figure 4:
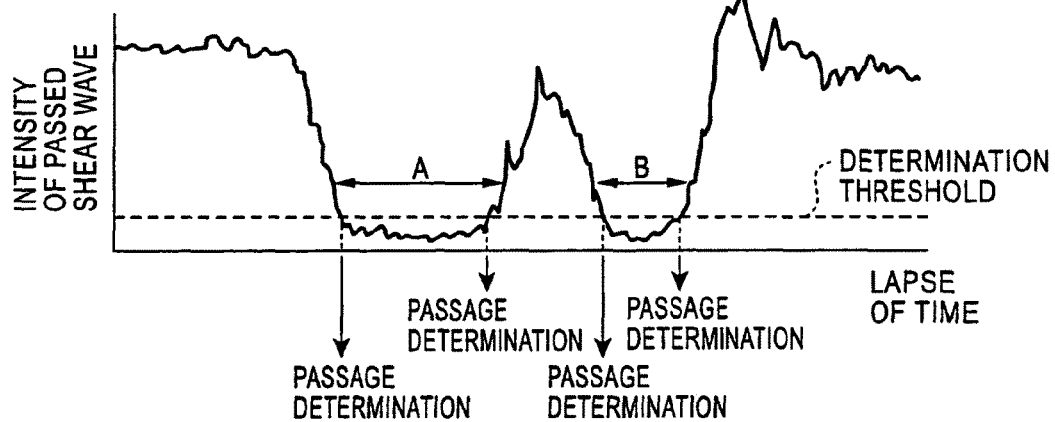
FIG. 4 shows one example of the operation of a crater end arrival detecting unit.

The operation of the crater end arrival detecting unit 11 will be described below with reference to FIG. 4. FIG. 4 shows one example of the operation of the crater end arrival detecting unit 11, and it is a chart obtained by detecting the intensity of the ultrasonic shear wave passage signal sent from the passed shear-wave intensity detecting unit 10 while changing the casting conditions over several tens minutes during the continuous casting operation.

As shown in FIG. 4, the intensity of the ultrasonic shear wave passage signal varies depending on changes of the casting conditions in the continuous casting operation. In ranges A and B of FIG. 4, the intensity of the passage signal is very small. This represents a state where the crater end 4 is positioned downstream of the installed position of the ultrasonic shear wave transmitter 6 and the ultrasonic shear wave receiver 8 in the casting direction. At the time when the intensity of the passage signal has crossed a predetermined determination threshold, the crater end arrival detecting unit 11 determines that the crater end 4 has passed the installed position of the ultrasonic shear wave sensor. The predetermined determination threshold may be a preset fixed value or a variable threshold set based on a value of a noise level obtained from a signal level in a time region where the ultrasonic shear wave passage signal does not appear. When the crater end arrival detecting unit 11 determines that the crater end 4 has passed the installed position of the ultrasonic shear wave sensor, it sends a timing signal to the crater end computing unit 13.

Figure 5:
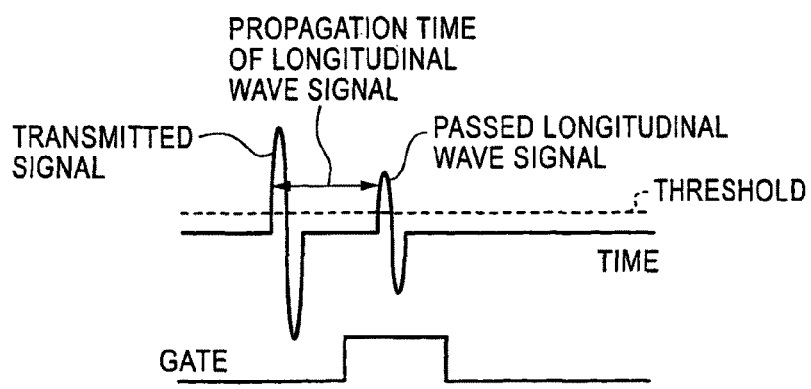
FIG. 5 shows the operation of a longitudinal-wave propagation time detecting unit.

The operation of the longitudinal-wave propagation time detecting unit 12 will be described below with reference to FIG. 5. FIG. 5 shows the operation of the longitudinal-wave propagation time detecting unit 12, and it illustrates the waveform of a received signal corresponding to one shot of transmitted signal. In FIG. 5, a first wave represents the transmitted signal electrically leaked into the ultrasonic longitudinal wave receiver 9, and a second wave represents the ultrasonic longitudinal wave passage signal. The longitudinal-wave propagation time detecting unit 12 detects a time from the timing of transmitting the transmitted signal to the timing at which the ultrasonic longitudinal wave passage signal appears. A method for detecting the ultrasonic longitudinal wave passage signal can be practiced by detecting the timing at which the passage signal exceeds a threshold as shown in FIG. 5, or by detecting the timing at which the passage signal is maximized within a gate. Such processing can be easily realized with a computing process by taking the waveform of the received signal into the computer after A/D conversion as in the passed shear-wave intensity detecting unit 10. In practice, since the transmitted signal is repeated at a cycle of several 10's Hz to several 100's Hz, it is effective, from the viewpoint of reducing influences of fluctuations due to noises, to determine the propagation time of the ultrasonic longitudinal wave signal after averaging each waveform, or to average the propagation time for each waveform.

Figure 6:
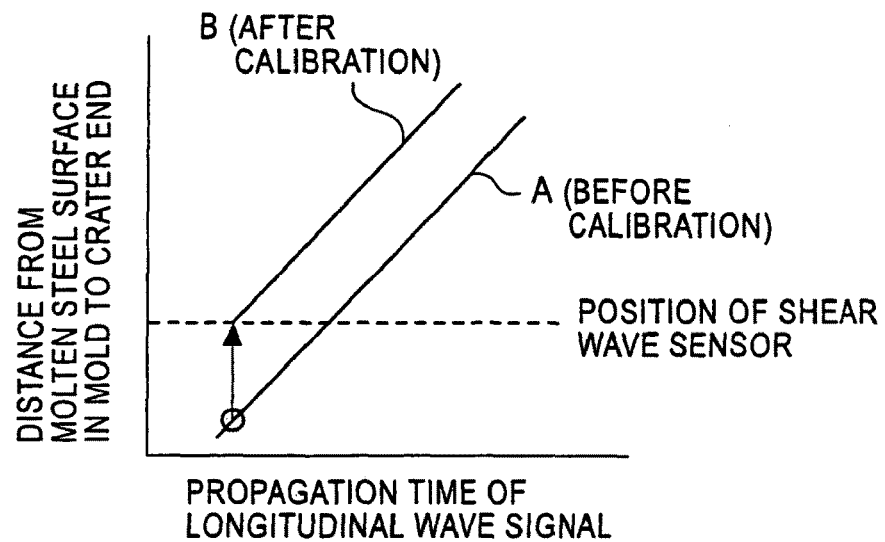
FIG. 6 shows the operation of a crater end computing unit in the first embodiment.

Finally, the operation of the crater end computing unit 13 will be described below with reference to FIG. 6. FIG. 6 shows the operation of the crater end computing unit 13 in the first embodiment, and it graphically illustrates an approximation formula for computing the crater end 4 from the propagation time of the ultrasonic longitudinal wave signal. The more downstream in the casting direction the crater end 4 is positioned with respect to the installed position of the ultrasonic longitudinal wave transmitter 7 and the ultrasonic longitudinal wave receiver 9, the larger is the thickness of the liquid phase 3 and the longer is the propagation time. Hence, the relationship between the propagation time and the distance from a molten steel surface 20 within the mold 101 to the crater end 4 is substantially proportional and is represented as shown in FIG. 6. In other words, the crater end 4 can be determined from the propagation time by using an approximation polynomial, e.g., a linear equation expressed by the following formula (2).

In the formula (2), CE is the distance from the molten steel surface 20 within the mold to the crater end 4, $\Delta t$ is the propagation time of the ultrasonic longitudinal wave, and $a_1$ and $a_0$ are coefficients of respective terms of the polynomial.

$$CE = a_1 \cdot \Delta t + a_0 \qquad (2)$$

In FIG. 6, a line indicated by A represents the approximation formula before calibration. When the timing signal corresponding to the passage determination of the crater end 4 is sent from the crater end arrival detecting unit 11 to the crater end computing unit 13, the crater end computing unit 13 computes the propagation time ($\Delta t_1$) of the ultrasonic longitudinal wave at that time and corrects the coefficient ($a_0$) in the formula (2) by using a formula (3), given below, so that the distance (CE) from the molten steel surface 20 within the mold to the crater end 4 is matched with the installed position of the ultrasonic shear wave sensor.

In the formula (3), $CE_1$ is the distance from the molten steel surface 20 within the mold to the installed position of the ultrasonic shear wave sensor, and $\Delta t_1$ is the propagation time of the ultrasonic longitudinal wave at the time when it is determined that the crater end 4 has passed the installed position of the ultrasonic shear wave sensor.

$$a_0 = CE_1 - a_1 \cdot \Delta t_1 \qquad (3)$$

As a result, the approximation formula for computing the crater end 4 is calibrated to be represented by, e.g., a line B after calibration shown in FIG. 6. After the calibration, the crater end 4 can be accurately detected online during the casting based on the propagation time of the ultrasonic longitudinal wave signal by using the calibrated approximation formula represented by B.

The calibration may be performed once whenever a slab having a new variety of chemical components is cast, or each time when the crater end 4 crosses the installed position of the ultrasonic shear wave sensor during the continuous casting operation, or at a proper time optionally decided at the operator's discretion.

Figure 7:
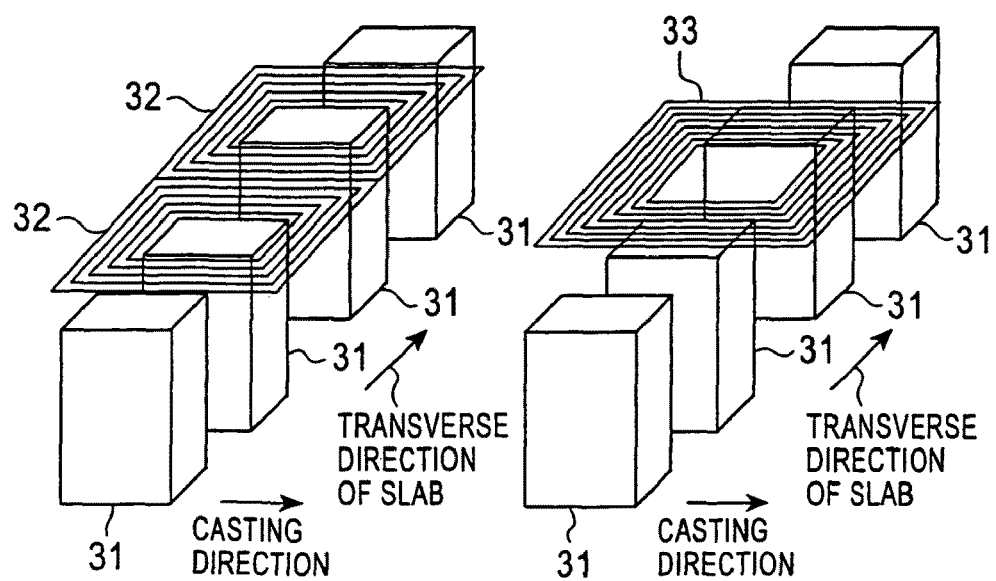
FIG. 7 shows the construction in which the electromagnetic ultrasonic sensor for generating and detecting the ultrasonic longitudinal wave and the ultrasonic shear wave at the same position has four magnetic poles.

As the electromagnetic ultrasonic sensor for generating and detecting the ultrasonic longitudinal wave and the ultrasonic shear wave at the same position, the above-described electromagnetic ultrasonic sensor, shown in FIG. 2, has three magnetic poles, but the number of magnetic poles can be made four or more. FIG. 7 shows the construction of another example in which the electromagnetic ultrasonic sensor for generating and detecting the ultrasonic longitudinal wave and the ultrasonic shear wave at the same position has four magnetic poles. The longitudinal wave coils 32 and the shear wave coil 33, which are actually arranged in overlapped relation, are separately illustrated in FIG. 7 for the sake of easier understanding of the coil arrangement with respect to the magnetic poles. The left side of FIG. 7 shows the arrangement of the longitudinal wave coils 32, and the right side shows the arrangement of the shear wave coil 33. As in the electromagnetic ultrasonic sensor shown in FIG. 2, each of the longitudinal wave coils 32 is arranged so as to wind the surrounding of an inner magnetic pole aside from its surface, and the shear wave coil 33 is arranged so as to overlie the magnetic pole surface. The number of magnetic poles is not limited to 4 and can be made more than 4. The arrangement having a larger number of magnetic poles provides an advantage that, because the intensity of a horizontal magnetic field for the longitudinal wave coil 32 is increased, sensitivity of the ultrasonic longitudinal wave is increased correspondingly and the positions for generating and detecting the ultrasonic shear wave and the ultrasonic longitudinal wave are substantially matched with each other.

When the crater end 4 is positioned upstream of the installed position of the ultrasonic longitudinal wave sensor, the ultrasonic longitudinal wave passes the solid phase 2 through an entire path. Also, the ultrasonic shear wave passes the solid phase 2 through an entire path because it is generated and detected at the same position as the ultrasonic longitudinal wave. In this case, the propagation time depends on the ultrasonic velocity in the solid phase 2. Since the ultrasonic velocity depends on the temperature of the solid phase 2, the propagation times of the ultrasonic longitudinal wave and the ultrasonic shear wave are changed depending on the temperature of the slab 1. On the other hand, when the distance from the crater end 4 to the installed position of the electromagnetic ultrasonic sensor varies, the temperature of the slab is changed. More specifically, as the crater end 4 is positioned upstream farther away from the installed position of the electromagnetic ultrasonic sensor, the temperature of the slab is lowered correspondingly. The lower the temperature of the slab, the higher is the ultrasonic velocity and hence the shorter is the propagation time.

Accordingly, when the crater end 4 is positioned upstream of the installed position of the ultrasonic longitudinal wave sensor, the relationship between the propagation time and the distance from the molten steel surface 20 to the crater end 4 has a similar tendency to that shown in FIG. 6. Comparing with the case where the crater end 4 is positioned downstream of the ultrasonic longitudinal wave sensor and the liquid phase 3 is contained in the propagation path, however, there are no influences of the liquid phase 3 in which the ultrasonic velocity is lower than that in the solid phase 2. Thus, even if the crater end 4 varies in the casting direction, the influence of such a variation upon the propagation time is small and so is a variation rate of the propagation time detected.

For that reason, the calculation formula used for computing the crater end 4 from the propagation time is preferably made different between when the crater end 4 is positioned upstream of the ultrasonic longitudinal wave sensor and when the crater end 4 is positioned downstream thereof.

More specifically, when the crater end 4 is positioned upstream of the ultrasonic longitudinal wave sensor, the crater end 4 can be determined by a method using an experiment formula (such as the formula shown in FIG. 6) which directly combines the propagation time and the crater end with each other, or by a method of estimating the inner temperature or the core temperature of the slab from the propagation time and then estimating the crater end from the estimated temperature value. On the other hand, when the crater end 4 is positioned downstream of the ultrasonic longitudinal wave sensor, the crater end 4 can be determined by a method using an experiment formula (such as the formula shown in FIG. 6) which directly combines the propagation time and the crater end with each other, or by a method of estimating the thickness of the solid phase 2 or the thickness of the liquid phase 3 from the propagation time and then estimating the crater end from the estimated thickness value. In the case of using the experiment formula such as shown in FIG. 6, the coefficients of the formula necessarily differ between when the crater end 4 is positioned upstream of the ultrasonic longitudinal wave sensor and when the crater end 4 is positioned downstream thereof.

In order to employ the different coefficients, it is required to determine whether the crater end 4 is positioned upstream or downstream of the installed position of the ultrasonic longitudinal wave sensor. To that end, the crater end arrival detecting unit 11 executes the following determination. If the intensity of the passed ultrasonic shear wave is larger than the threshold, the crater end arrival detecting unit 11 determines that the crater end 4 is positioned in the upstream side. Conversely, if the intensity of the passed ultrasonic shear wave is not larger than the threshold, it determines that the crater end 4 is positioned in the downstream side. Then, the crater end arrival detecting unit 11 sends a corresponding signal to the crater end computing unit 13. The crater end computing unit 13 selects, based on the determination result, the calculation formula used for computing the crater end 4 and computes the crater end 4 by using the selected calculation formula.

In the case of determining the crater end 4 from the propagation time of the ultrasonic shear wave signal when the crater end 4 is positioned upstream of the installed position of the ultrasonic shear wave sensor, a shear-wave propagation time detecting unit having the function similar to that of the longitudinal-wave propagation time detecting unit 12 has to be disposed at the output side of the ultrasonic shear wave sensor.

Figure 8:
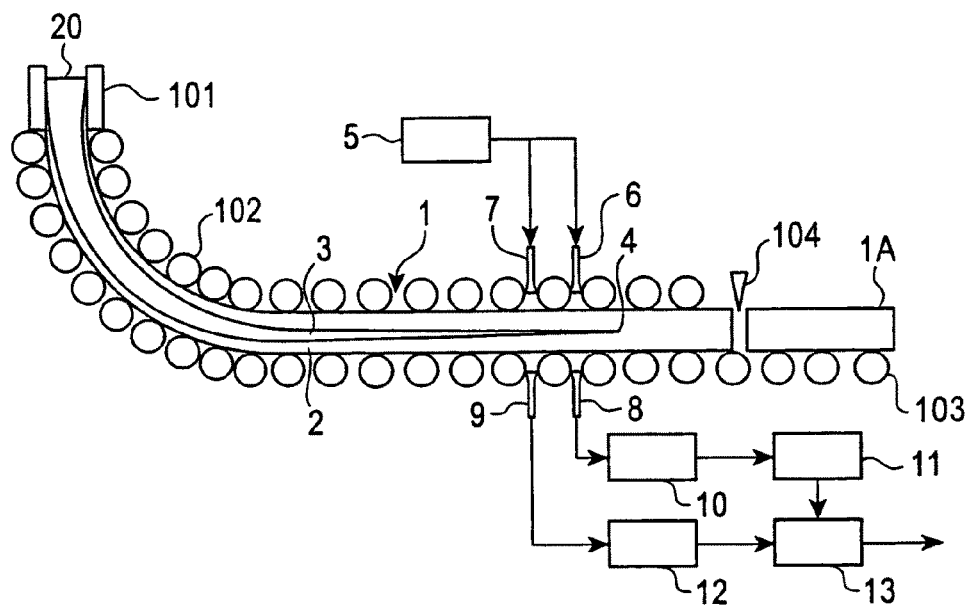
FIG. 8 shows a second embodiment of the present invention.

A second embodiment of the method and apparatus for detecting the crater end from the propagation time of the ultrasonic longitudinal wave signal measured by the ultrasonic longitudinal wave sensor will be described below. FIG. 8 shows a second embodiment of the present invention, and it is a schematic view of a slab continuous casting machine provided with a crater end detector according to the present invention, in which an ultrasonic shear wave sensor and an ultrasonic longitudinal wave sensor are separately disposed in two points apart from each other in the casting direction of the continuous casting machine but at the same position in the transverse direction of the slab.

In the second embodiment, as shown in FIG. 8, the ultrasonic shear wave sensor made up of the ultrasonic shear wave transmitter 6 and the ultrasonic shear wave receiver 8 and the ultrasonic longitudinal wave sensor made up of the ultrasonic longitudinal wave transmitter 7 and the ultrasonic longitudinal wave receiver 9 are separately disposed in two points apart from each other in the casting direction. In this case, the ultrasonic shear wave sensor and the ultrasonic longitudinal wave sensor are not required to be the above-described sensor for generating and detecting the ultrasonic longitudinal wave and the ultrasonic shear wave at the same position, shown in FIG. 2, and can be each constituted as an ordinary electromagnetic ultrasonic sensor. Of course, the electromagnetic ultrasonic sensor shown in FIG. 2 can also be employed.

However, since the crater end 4 sometimes differs in the transverse direction of the slab 1 in the slab continuous casting machine, the ultrasonic shear wave sensor and the ultrasonic longitudinal wave sensor have to be disposed within such a range in the transverse direction that a relative change in positions of the crater end 4 in the transverse direction, which are detected by the ultrasonic shear wave sensor and the ultrasonic longitudinal wave sensor, can be regarded substantially not present. More specifically, when the secondary cooling is appropriate and the shape of the crater end 4 in the transverse direction can be regarded flat, as described above, the ultrasonic shear wave sensor and the ultrasonic longitudinal wave sensor may be apart from each other by a distance of several 100's mm. Conversely, when the shape of the crater end 4 in the transverse direction is changed to a large extent, the distance between those two sensors has to be kept within several 10's mm. Accordingly, it is required to set the distance between those two sensors within several 10's mm in order to be adapted for any of those cases.

Further, the narrower the spacing between the installed position of the ultrasonic shear wave sensor and the installed position of the ultrasonic longitudinal wave sensor, the higher is the detection accuracy. Conversely, the wider the spacing between those two sensors, the lower is the detection accuracy. For that reason, the spacing between the sensors is preferably not larger than about 5 m. Also, since the propagation time of the ultrasonic longitudinal wave signal detected by the ultrasonic longitudinal wave sensor is changed in a highly sensitive way when the liquid phase 3 is contained, as described above, higher accuracy is obtained in a state where the crater end 4 is positioned downstream of the ultrasonic longitudinal wave sensor. Therefore, the ultrasonic longitudinal wave sensor is preferably disposed upstream of the ultrasonic shear wave sensor in the casting direction.

The other construction is the same as that in the first embodiment shown in FIG. 1. The same components as those in FIG. 1 are denoted by the same reference numerals and a description of those components is omitted here.

The passed shear-wave intensity detecting unit 10, the crater end arrival detecting unit 11, the longitudinal-wave propagation time detecting unit 12 and the crater end computing unit 13 operate in a similar manner to that in the first embodiment. When the timing signal corresponding to the determination as to the passage of the crater end 4 is sent from the crater end arrival detecting unit 11 to the crater end computing unit 13, the crater end computing unit 13 computes the propagation time ($\Delta t_1$) of the ultrasonic longitudinal wave at that time and corrects the coefficient ($a_0$) based on the above-described formula (3) so that the distance (CE) from the molten steel surface 20 to the crater end 4 is matched with the installed position of the ultrasonic shear wave sensor. After calibrating the polynomial used for computing the crater end 4, the crater end 4 can be accurately detected online during the casting based on the propagation time of the ultrasonic longitudinal wave signal by using the calibrated approximation formula.

The timing of the calibration and change of the calculation formula used for computing the crater end 4 depending on whether the crater end 4 is positioned upstream of the ultrasonic longitudinal wave sensor are decided and performed in the manner described above in connection with first embodiment.

While the installed position of the ultrasonic shear wave sensor is downstream of the installed position of the ultrasonic longitudinal wave sensor in FIG. 8, the arrangement may be reversed such that the ultrasonic shear wave sensor is positioned upstream of the ultrasonic longitudinal wave sensor. In that case, however, because the accuracy in detecting the crater end 4 positioned upstream of the ultrasonic longitudinal wave sensor by using the ultrasonic longitudinal wave sensor is not so high, it is desired to, after detection of arrival of the crater end 4 by the ultrasonic shear wave sensor, calibrate the polynomial in consideration of the casting speed at the time when the crater end 4 is estimated to reach the installed position of the ultrasonic longitudinal wave sensor. That calibration ensures high accuracy.

Figure 9:
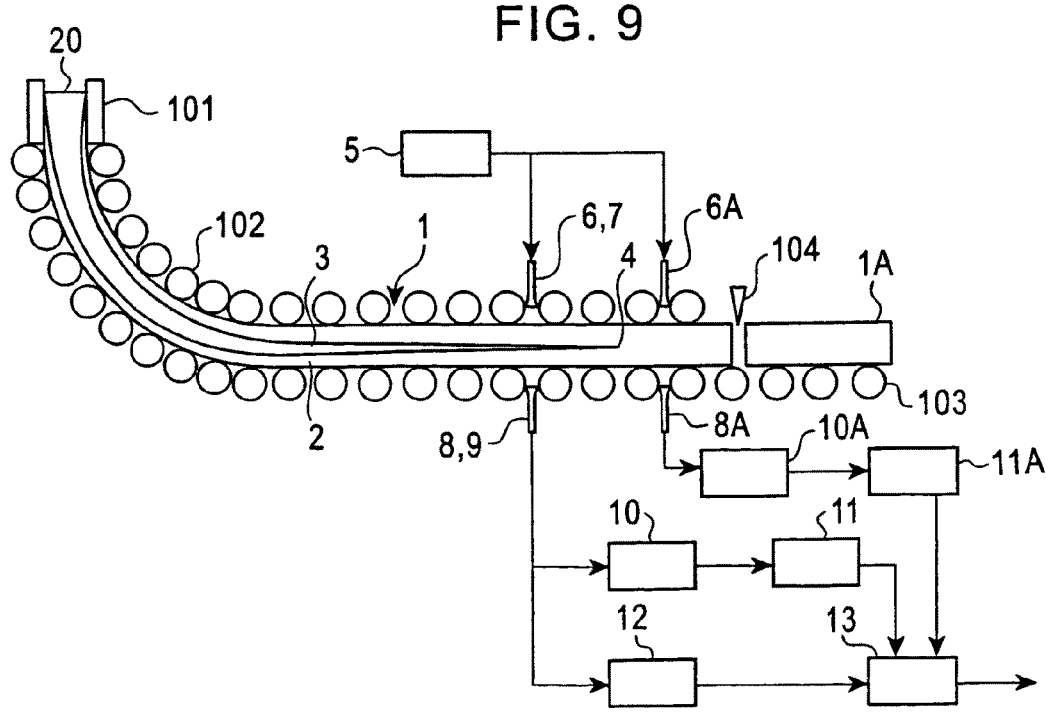
FIG. 9 shows a third embodiment of the present invention.

A third embodiment of the method and apparatus for detecting the crater end from the propagation time of the ultrasonic longitudinal wave measured by the ultrasonic longitudinal wave sensor will be described below. FIG. 9 shows a third embodiment of the present invention, and it is a schematic view of a slab continuous casting machine provided with a crater end detector according to the present invention, in which a second ultrasonic shear wave sensor is installed at a point apart from the electromagnetic ultrasonic sensor in the casting direction of the continuous casting machine but at the same position in the transverse direction of the slab.

In the third embodiment, as shown in FIG. 9, a second ultrasonic shear wave sensor made up of an ultrasonic shear wave transmitter 6A and an ultrasonic shear wave receiver 8A is installed downstream of the installed position of the electromagnetic ultrasonic sensor in the first embodiment, which is made up of the ultrasonic shear wave transmitter 6, the ultrasonic shear wave receiver 8, the ultrasonic longitudinal wave transmitter 7, and the ultrasonic longitudinal wave receiver 9 and is capable of generating and detecting the ultrasonic longitudinal wave and the ultrasonic shear wave. In this case, the second ultrasonic shear wave sensor is not required to be the above-described sensor for generating and detecting the ultrasonic longitudinal wave and the ultrasonic shear wave at the same position, shown in FIG. 2, and can be constituted as an ordinary electromagnetic ultrasonic sensor. Of course, the electromagnetic ultrasonic sensor shown in FIG. 2 can also be employed. Further, to avoid the influence of change of the crater end 4 in the transverse direction of the slab, the second ultrasonic shear wave sensor is installed at the same position in the transverse direction of the slab as the ultrasonic shear wave sensor (hereinafter referred to as a "first shear wave sensor") made up of the ultrasonic shear wave transmitter 6 and the ultrasonic shear wave receiver 8. A signal received by the ultrasonic shear wave receiver 8A is sent to a passed shear-wave intensity detecting unit 10A, and a signal detected by the passed shear-wave intensity detecting unit 10A is sent to a crater end arrival detecting unit 11A. The passed shear-wave intensity detecting unit 10A and the crater end arrival detecting unit 11A have the same functions as those of the passed shear-wave intensity detecting unit 10 and the crater end arrival detecting unit 11 in the first embodiment. Namely, when the crater end 4 passes the installed position of the second ultrasonic shear wave sensor, the crater end arrival detecting unit 11A sends a timing signal to the crater end computing unit 13.

Further, if the spacing between the installed position of the second ultrasonic shear wave sensor and the installed position of the first shear wave sensor is too narrow, the calibration accuracy cannot be increased. From the viewpoint of increasing the calibration accuracy, therefore, the appropriate spacing between those two sensors is in the range of about 2 m to 10 m. The other construction is the same as that in the first embodiment shown in FIG. 1. The same components as those in FIG. 1 are denoted by the same reference numerals and a description of those components is omitted here.

The passed shear-wave intensity detecting unit 10, the crater end arrival detecting unit 11, and the longitudinal-wave propagation time detecting unit 12 operate in a similar manner to that in the first embodiment, but the crater end computing unit 13 operates in a different manner. Therefore, the operation of the crater end computing unit 13 will be described below with reference to FIG. 10.

Figure 10:
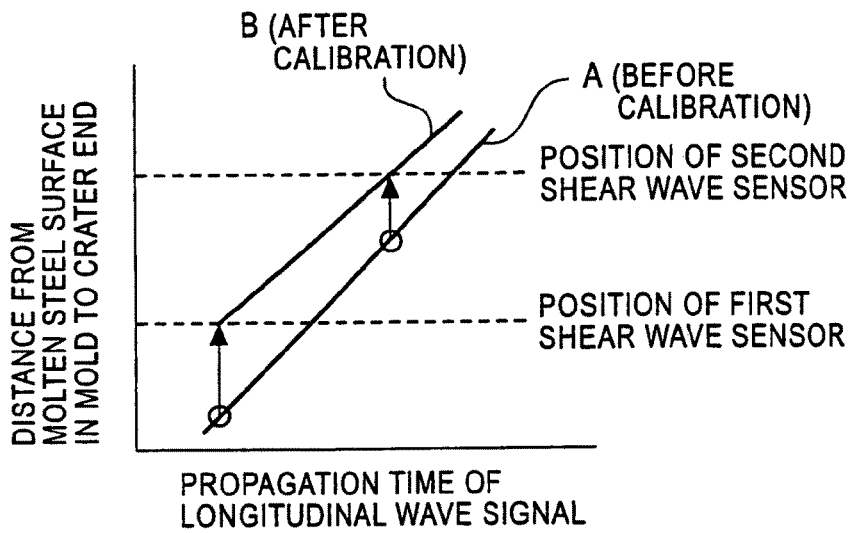
FIG. 10 shows the operation of a crater end computing unit in the third embodiment.

FIG. 10 shows the operation of the crater end computing unit 13 in the third embodiment, and it graphically illustrates an approximation formula for computing the crater end 4 from the propagation time of the ultrasonic longitudinal wave signal. It is here assumed that, as in the first embodiment, the crater end 4 is computed from the propagation time of the ultrasonic longitudinal wave signal by using the formula (2). A line A in FIG. 10 represents the approximation formula before calibration.

When a timing signal corresponding to the determination as to the passage of the crater end 4 at the position of the first shear wave sensor is sent from the crater end arrival detecting unit 11 to the crater end computing unit 13, the crater end computing unit 13 stores a propagation time ($\Delta t_1$) of the ultrasonic longitudinal wave signal at that time. Then, the casting speed, the intensity of the secondary cooling, etc. are changed such that the crater end 4 is extended to the downstream side in the casting direction. When the crater end 4 passes the installed position of the second ultrasonic shear wave sensor, a timing signal corresponding to the determination as to the passage of the crater end 4 is sent from the crater end arrival detecting unit 11A to the crater end computing unit 13, and the crater end computing unit 13 computes a propagation time ($\Delta t_2$) of the ultrasonic longitudinal wave signal at that time. Further, the crater end computing unit 13 solves a simultaneous equation of formulae (4) and (5) given below, thereby correcting the constants ($a_1$) and ($a_0$) of the above-described formula (2). In the formulae (4) and (5), $CE_1$ is the distance from the molten steel surface 20 within the mold to the installed position of the first shear wave sensor, $\Delta t_1$ is the propagation time of the ultrasonic longitudinal wave signal at the time when it is determined that the crater end 4 has passed the installed position of the first shear wave sensor, $CE_2$ is the distance from the molten steel surface 20 within the mold to the installed position of the second ultrasonic shear wave sensor, and $\Delta t_1$ is the propagation time of the ultrasonic longitudinal wave signal at the time when it is determined that the crater end 4 has passed the installed position of the second ultrasonic shear wave sensor.

$$CE_1 = a_1 \cdot \Delta t_1 + a_0 \quad \quad (4)$$

$$CE_2 = a_1 \cdot \Delta t_2 + a_0 \quad \quad (5)$$

As a result, the approximation formula for computing the crater end 4 is calibrated to be represented by, e.g., a line B shown in FIG. 10. After the calibration, the crater end 4 can be accurately detected online based on the propagation time of the ultrasonic longitudinal wave signal during the casting by using the calibrated approximation formula represented by B. In this case, the crater end 4 can be detected with higher accuracy than that in the first embodiment.

The timing of the calibration and change of the calculation formula used for computing the crater end 4 depending on whether the crater end 4 is positioned upstream of the ultrasonic longitudinal wave sensor are decided and performed in the manner described above in connection with the first embodiment.

Figure 11:
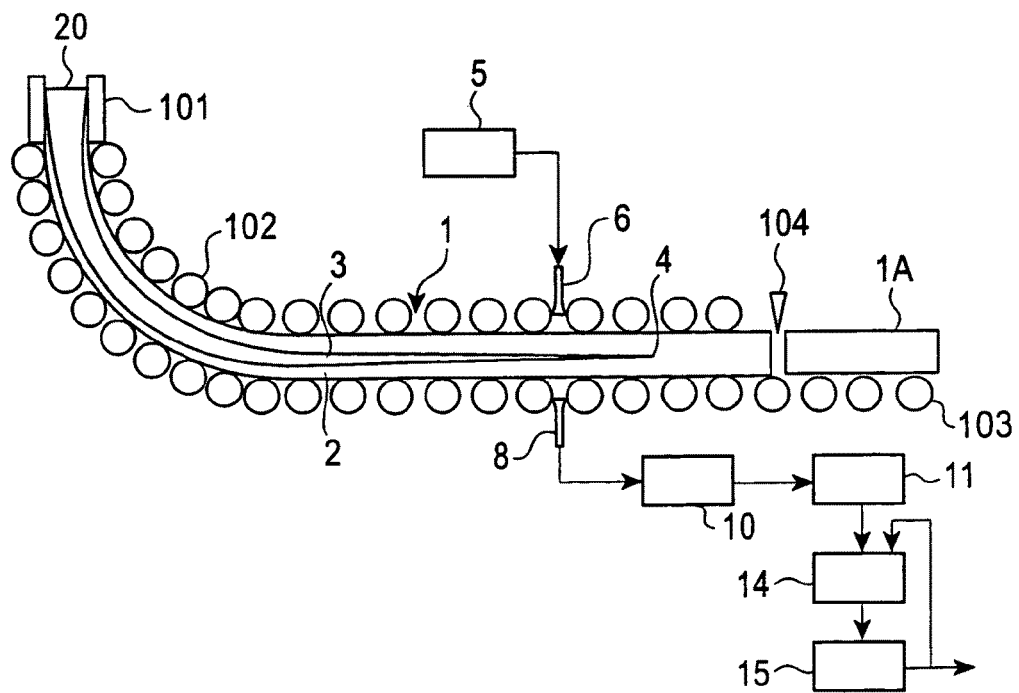
FIG. 11 shows a fourth embodiment of the present invention.

The method and apparatus for detecting the crater end from the casting conditions and the values of physical properties by calculation based on the heat condition equation will be described below. FIG. 11 shows a fourth embodiment of the present invention, and it is a schematic view of a slab continuous casting machine provided with a crater end detector according to the present invention.

The crater end detector according to the present invention for detecting the crater end 4 from the casting conditions and the values of physical properties by calculation based on the heat condition equation comprises, as shown in FIG. 11, an ultrasonic shear wave sensor made up of an ultrasonic shear wave transmitter 6 and an ultrasonic shear wave receiver 8 disposed in opposed relation with a slab 1 between them, an ultrasonic transmitting unit 5 which is an electric circuit for supplying an electric signal to the ultrasonic shear wave transmitter 6, thereby causing an ultrasonic wave to be transmitted to the slab 1, a passed shear-wave intensity detecting unit 10 and a crater end arrival detecting unit 11 for processing a signal received by the ultrasonic shear wave receiver 8, a physical property value storage unit 14 for storing the values of physical properties used in the calculation based on the heat condition equation, and a heat condition equation unit 15 for executing the calculation based on the heat condition equation.

The passed shear-wave intensity detecting unit 10 detects the intensity of the ultrasonic shear wave signal received by the ultrasonic shear wave receiver 8. The crater end arrival detecting unit 11 determines whether the crater end 4 is positioned upstream or downstream of the installed position of the ultrasonic shear wave transmitter 6 and the ultrasonic shear wave receiver 8 in the casting direction, based on variations of an ultrasonic shear wave passage signal detected by the passed shear-wave intensity detecting unit 10. The processing in the passed shear-wave intensity detecting unit 10 and the crater end arrival detecting unit 11 is executed by a computer. Though not shown, an ultrasonic signal amplifier, an A/D converter for taking a signal waveform into the computer, etc. are required between the ultrasonic shear wave receiver 8 and the computer. Additionally, the physical property value storage unit 14 and the heat condition equation unit 15 are also constituted by the computer.

A mariner for processing the received signal will be described below. First, the operation of the passed shear-wave intensity detecting unit 10 will be described. Because the operation of the passed shear-wave intensity detecting unit 10 is basically the same as that of the passed shear-wave intensity detecting unit 10 in the first embodiment, the following description is made with reference to FIG. 3.

In FIG. 3, a first wave is generated upon the transmitted signal electrically leaking into the ultrasonic shear wave receiver 8, and a second wave represents the ultrasonic shear wave passage signal. Because a position on the time base where the ultrasonic shear wave passage signal appears is roughly known from the thickness of the slab 1, the approximate temperature of the slab 1, and the ultrasonic velocity of the shear wave, a gate for taking out the signal only at that position is provided to determine a maximum value of the signal within the gate. Such processing can be easily realized with a computing process by taking the waveform of the received signal into the computer after A/D conversion. The maximum value of the signal can be determined as an absolute value on the basis of 0 V or as a peak-to-peak value. In practice, since the transmitted signal is repeated at a cycle of several 10's Hz to several 100's Hz, it is effective, from the viewpoint of reducing influences of fluctuations due to noises, to determine the intensity of the passed ultrasonic shear wave after averaging each waveform, or to average the intensity of the passed ultrasonic shear wave for each waveform.

Figure 12:
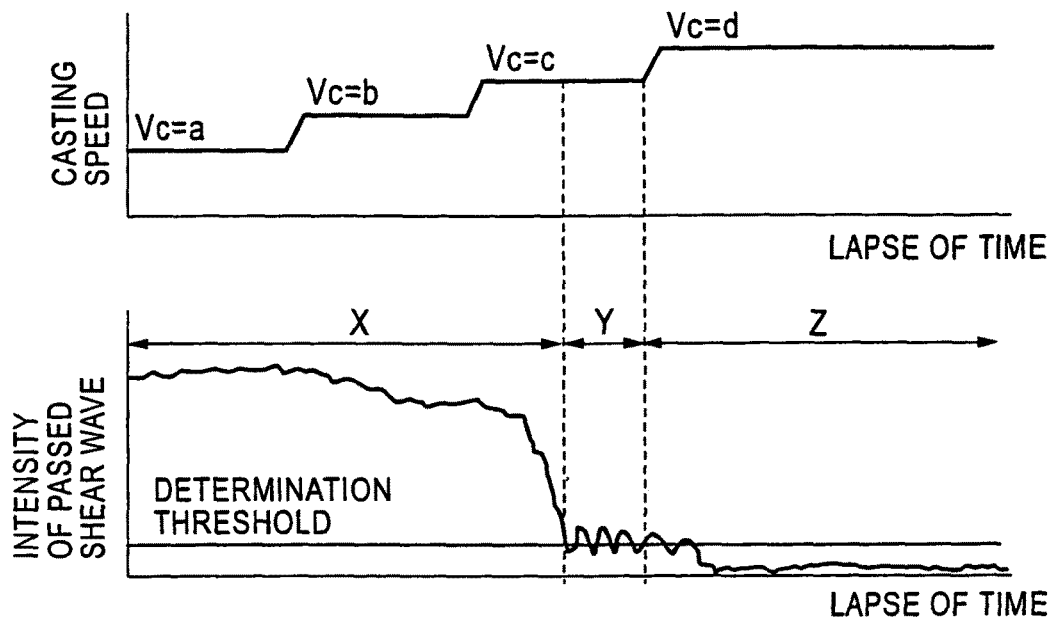
FIG. 12 shows another example of the operation of the crater end arrival detecting unit.

The operation of the crater end arrival detecting unit 11 will be described below with reference to FIG. 12. FIG. 12 shows another example of the operation of the crater end arrival detecting unit 11, and it is a chart showing the intensity of the passed ultrasonic shear wave when the casting speed is increased in 4 stages of a to d step by step. Within a range X in FIG. 12, the intensity of the passed ultrasonic shear wave is larger than a determination threshold, and therefore it is determined that the slab 1 is solidified at the installed position of the ultrasonic shear wave sensor. When the casting speed is increased to c and comes into a range Y, the intensity of the passed ultrasonic shear wave becomes smaller than the determination threshold, and therefore it is determined that the crater end 4 has reached the installed position of the ultrasonic shear wave sensor. In the range Y corresponding to a stationary region of the casting speed c, the intensity of the passed ultrasonic shear wave is varied up and down about the threshold. This indicates that the crater end 4 is averagely positioned at the installed position of the ultrasonic shear wave sensor under the relevant casting conditions and is slightly moved upstream and downstream of the ultrasonic shear wave sensor due to slight fluctuations. In a range Z where the casting speed is further increased, the intensity of the passed ultrasonic shear wave is always smaller than the determination threshold, and therefore it is determined that the slab 1 is in a liquid state at the installed position of the ultrasonic shear wave sensor. When the crater end arrival detecting unit 11 thus determines that the crater end 4 has passed the installed position of the ultrasonic shear wave sensor, it sends a timing signal to the physical property value storage unit 14.

Finally, a manner for executing the calculation based on the heat condition equation and a manner for executing calibration will be described below. The physical property value storage unit 14 stores the values of physical properties used in the calculation based on the heat condition equation. The values of physical properties mainly include the density of the slab 1, the enthalpy, the thermal conductivity, the solidus temperature, heat removed in the mold 101, the heat transfer coefficient in the secondary cooling zone, and the temperature of molten steel. In addition to those values, the casting conditions include the thickness and width of the slab 1, the casting speed, the chemical components, etc., and are provided to the heat condition equation unit 15 along with the values of physical properties. The heat condition equation unit 15 calculates temperature changes successively in the withdrawing direction of the slab 1 starting from the temperature of the molten steel. The crater end 4 can be obtained as a position where the core temperature of the slab 1 intersects the solidus.

Figure 13:
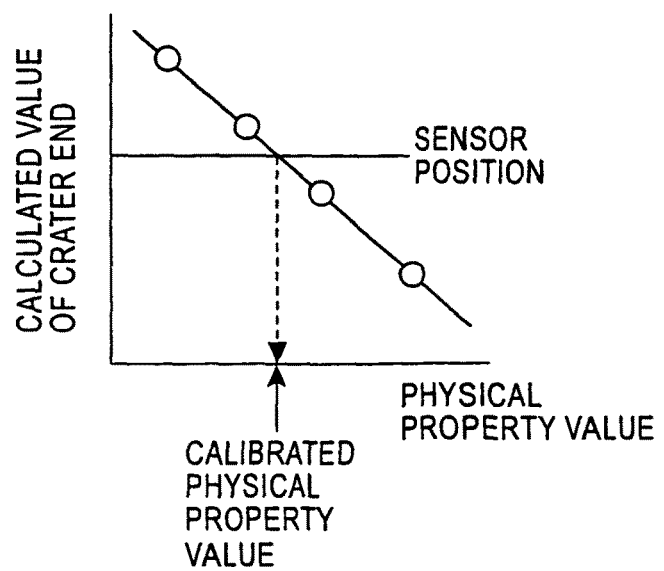
FIG. 13 shows the behavior of the crater end when a thermal conductivity used in calculation based on the heat condition equation is changed.

In accordance with the timing signal corresponding to the passage of the crater end 4 and sent from the crater end arrival detecting unit 11, the heat condition equation unit 15 executes the calculation based on the heat condition equation by using the values of physical properties inputted in the physical property value storage unit 14 and the casting conditions when the crater end 4 is matched with the installed position of the ultrasonic shear wave sensor, and then changes any of the values of physical properties so that the crater end obtained by the calculation based on the heat condition equation is matched with the installed position of the ultrasonic shear wave sensor. More specifically, the crater end is determined by the calculation based on the heat condition equation while changing, e.g., the thermal conductivity in several stages. Then, as shown in FIG. 13, the thermal conductivity is determined under the condition that the crater end determined by the calculation based on the heat condition equation is matched with the installed position of the ultrasonic shear wave sensor. FIG. 13 shows the behavior of the crater end when the thermal conductivity used in the calculation based on the heat condition equation is changed, and it graphically illustrates the fact that the distance from the molten steel surface 20 to the crater end 4 is shortened as the thermal conductivity is increased.

While the thermal conductivity is employed, by way of example, in the above description, the value of another physical property, such as the heat transfer coefficient of the secondary cooling zone, can also be of course employed as the physical property value used for the calibration. The calibrated physical property value is inputted from the heat condition equation unit 15 to the physical property value storage unit 14 and stored therein. Thereafter, the calculation based on the heat condition equation is executed using the calibrated physical property value. In such a way, the heat condition equation is calibrated.

The calibration may be performed once whenever a slab having a new variety of chemical components is cast, or each time when the crater end 4 crosses the installed position of the ultrasonic shear wave sensor during the continuous casting operation, or at a proper time optionally decided at the operator's discretion.

Figure 14:
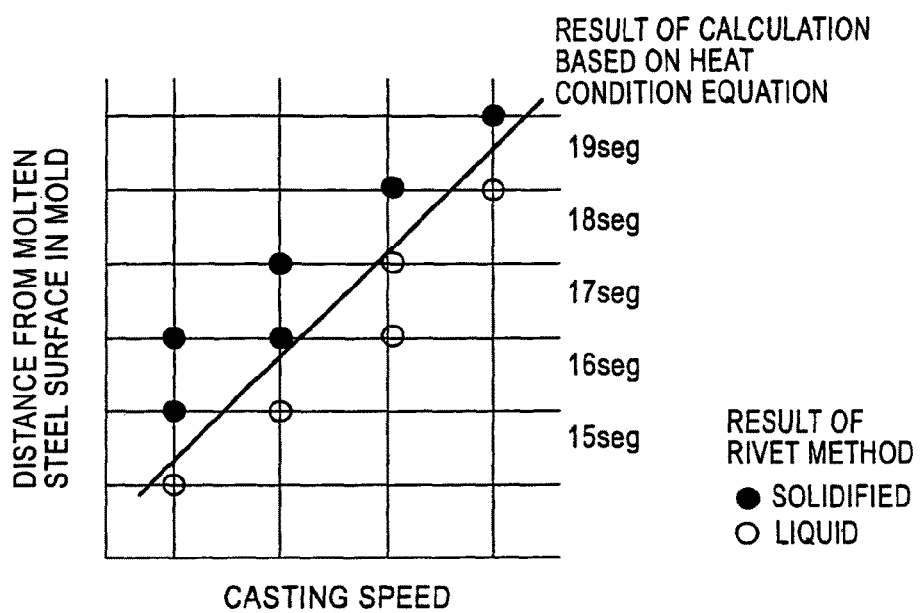
FIG. 14 comparatively shows the crater end obtained by the calculation based on the heat condition equation and the crater end confirmed by using the rivet method.

FIG. 14 comparatively shows the crater end determined by the calculation based on the heat condition equation calibrated while changing the casting speed in several stages and the results obtained by driving metal-made rivets into the slab 1 and determining whether the slab 1 is solidified or liquid at plural points in the lengthwise direction of the slab when the casting speed is similarly changed in several stages during the operation. As seen from FIG. 14, the crater end determined by the calculation based on the heat condition equation is well matched with the crater end confirmed by using the rivet method. Thus, it has been proved that the crater end 4 can be estimated with high accuracy according to the present invention.

Figure 15:
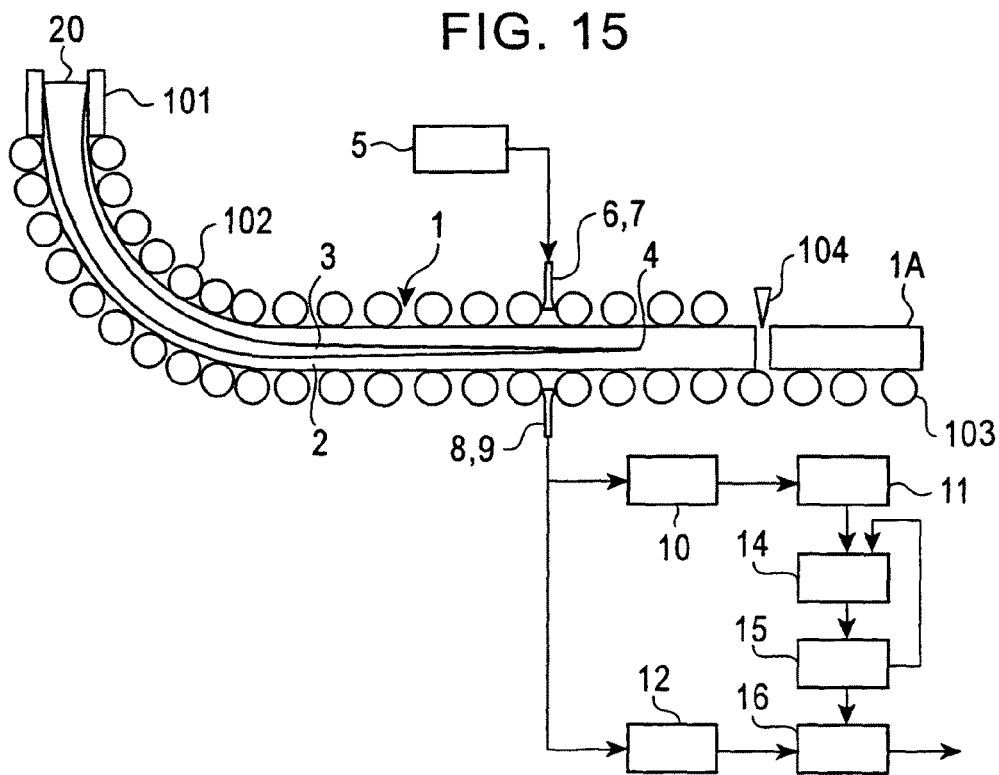
FIG. 15 shows a fifth embodiment of the present invention.

A fifth embodiment related to the method and apparatus for detecting the crater end from the casting conditions and the values of physical properties by calculation based on the heat condition equation will be described below. FIG. 15 shows a fifth embodiment of the present invention, and it is a schematic view of a slab continuous casting machine provided with a crater end detector according to the present invention.

As shown in FIG. 15, the crater end detector of the fifth embodiment comprises an ultrasonic shear wave sensor made up of an ultrasonic shear wave transmitter 6 and an ultrasonic shear wave receiver 8 disposed in opposed relation with the slab 1 between them, an ultrasonic longitudinal wave sensor made up of an ultrasonic longitudinal wave transmitter 7 and an ultrasonic longitudinal wave receiver 9 disposed in opposed relation with the slab 1 between them, an ultrasonic transmitting unit 5 which is an electric circuit for supplying an electric signal to each of the ultrasonic shear wave transmitter 6 and the ultrasonic longitudinal wave transmitter 7, thereby causing ultrasonic waves to be transmitted to the slab 1, a passed shear-wave intensity detecting unit 10 and a crater end arrival detecting unit 11 for processing a signal received by the ultrasonic shear wave receiver 8, a longitudinal-wave propagation time detecting unit 12 for processing a signal received by the ultrasonic longitudinal wave receiver 9, a physical property value storage unit 14 for storing the values of physical properties used in the calculation based on the heat condition equation, a heat condition equation unit 15 for executing the calculation based on the heat condition equation, and a crater end estimating unit 16 for processing signals from the longitudinal-wave propagation time detecting unit 12 and the heat condition equation unit 15. In this embodiment, the ultrasonic shear wave sensor and the ultrasonic longitudinal wave sensor are constituted as a sensor for generating and detecting the ultrasonic longitudinal wave and the ultrasonic shear wave at the same position, shown in FIG. 2, but they can also be constituted as ordinary electromagnetic ultrasonic sensors.

The longitudinal-wave propagation time detecting unit 12 detects the propagation time of the ultrasonic longitudinal wave signal, which is passed through the slab 1, from the signal received by the ultrasonic longitudinal wave receiver 9. The crater end estimating unit 16 determines a relationship between the propagation time of the ultrasonic longitudinal wave signal detected by the longitudinal-wave propagation time detecting unit 12 and the crater end computed by the heat condition equation unit 15, and indirectly estimates the crater end 4 from the propagation time of the ultrasonic longitudinal wave signal based on the determined relationship. The longitudinal-wave propagation time detecting unit 12 and the crater end estimating unit 16 are constituted by a computer. The other components, i.e., the passed shear-wave intensity detecting unit 10, the crater end arrival detecting unit 11, the physical property value storage unit 14, and the heat condition equation unit 15, are the same as those in the fourth embodiment and have the same functions. A description of those components is omitted here.

A manner of processing the received signal will be described below. Manners of processing signals in the passed shear-wave intensity detecting unit 10, the crater end arrival detecting unit 11, the physical property value storage unit 14, and the heat condition equation unit 15 are the same as those in the fourth embodiment, and therefore a description of those manners is omitted here.

Because the operation of the longitudinal-wave propagation time detecting unit 12 is basically the same as that of the longitudinal-wave propagation time detecting unit 12 in the first embodiment, the following description is made with reference to FIG. 5. In FIG. 5, a first wave represents the transmitted signal electrically leaked into the ultrasonic longitudinal wave receiver 9, and a second wave represents the ultrasonic longitudinal wave passage signal. The longitudinal-wave propagation time detecting unit 12 detects a time from the timing of transmitting the transmitted signal to the timing at which the ultrasonic longitudinal wave passage signal appears. A method for detecting the ultrasonic longitudinal wave passage signal can be practiced by detecting the timing at which the passage signal exceeds a threshold as shown in FIG. 5, or by detecting the timing at which the passage signal is maximized within a gate. Such processing can be easily realized with a computing process by taking the waveform of the received signal into the computer after A/D conversion as in the passed shear-wave intensity detecting unit 10. In practice, since the transmitted signal is repeated at a cycle of several 10's Hz to several 100's Hz, it is effective, from the viewpoint of reducing influences of fluctuations due to noises, to determine the propagation time of the ultrasonic longitudinal wave signal after averaging each waveform, or to average the propagation time for each waveform.

Figure 16:
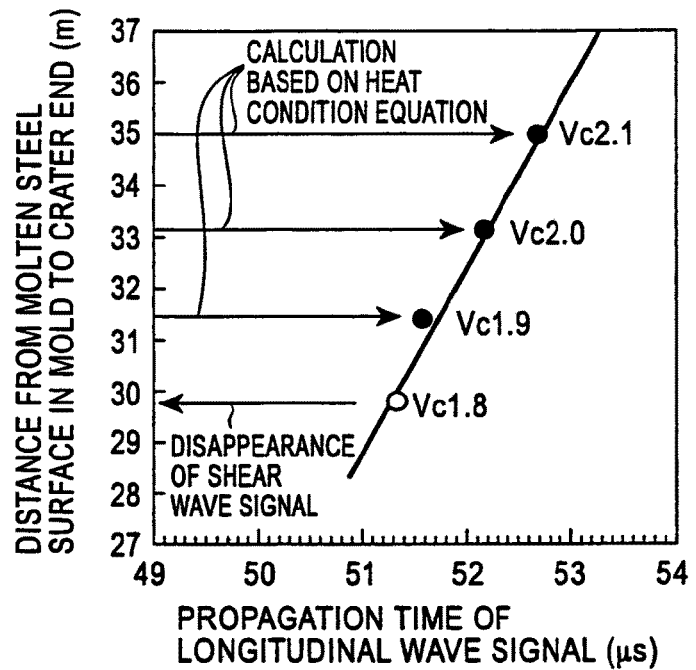
FIG. 16 shows an example of the processing function of a crater end estimating unit.

Finally, the operation of the crater end estimating unit 16 will be described below with reference to FIG. 16. FIG. 16 shows one example of the processing function of the crater end estimating unit 16, and it graphically illustrates an approximation formula for computing the crater end 4 from the propagation time of the ultrasonic longitudinal wave, which is prepared by the crater end estimating unit 16. In FIG. 16, the horizontal axis represents the value of the propagation time measured by the longitudinal-wave propagation time detecting unit 12, and the vertical axis represents the distance from the molten steel surface 20 to the crater end 4. Vc in FIG. 16 denotes the casting speed.

It is here assumed that the ultrasonic shear wave sensor is installed at a position apart from the molten steel surface 20 by a distance of 29.7 m and a signal similar to that obtained in the range Y in FIG. 12 is obtained in a stationary region at Vc=1.8 m/minute, for example. Since the crater end 4 under those casting conditions is positioned at 29.7 m from the molten steel surface 20, a white circle can be plotted as shown in FIG. 16 by comparing with the propagation time measured by the longitudinal-wave propagation time detecting unit 12 at that time. Further, at that time, the heat condition equation unit 15 executes the calculation based on the heat condition equation by using the casting conditions and the values of physical properties inputted in the physical property value storage unit 14, and calibrates any of the values of physical properties used in the calculation based on the heat condition equation so that the crater end 4 determined by the calculation based on the heat condition equation is given as 29.7 m. Then, by using the calibrated physical property value, the heat condition equation unit 15 determines the crater ends at Vc=1.9 m/minute, 2.0 m/minute and 2.1 m/minute, for example, by the calculation based on the heat condition equation. The calibrated physical property value is stored in the physical property value storage unit 14. Further, the casting operation is performed at each of the casting speeds of Vc=1.9 m/minute, 2.0 m/minute and 2.1 m/minute at which the calculation based on the heat condition equation has been executed to determine the crater end, and the longitudinal-wave propagation time detecting unit 12 measures the propagation time of the ultrasonic longitudinal wave signal in a stationary region at each casting speed. Black circles in FIG. 16 are each obtained by plotting the measured propagation time of the ultrasonic longitudinal wave signal and the crater end determined by the calculation based on the heat condition equation. By preparing an approximation formula or a table representing the relationship between the propagation time of the ultrasonic longitudinal wave signal and the crater end from the thus-plotted points, it becomes possible to determine the crater end 4 from the propagation time of the ultrasonic longitudinal wave signal. The approximation formula may be a linear or polynomial equation.

Preferably, whenever the physical property value used in the calculation based on the heat condition equation is calibrated, the approximation formula or the table representing the relationship between the propagation time and the crater end determined by the calculation based on the heat condition equation is updated. The calibration of the physical property value used in the calculation based on the heat condition equation may be performed once whenever a slab having a new variety of chemical components is cast, or each time when the crater end 4 crosses the installed position of the ultrasonic shear wave sensor during the continuous casting operation, or at a proper time optionally decided at the operator's discretion. While the ultrasonic shear wave sensor and the ultrasonic longitudinal wave sensor are installed at the same position in the fifth embodiment, those sensors may be installed at different positions apart from each other in the slab withdrawing direction.

Figure 17:
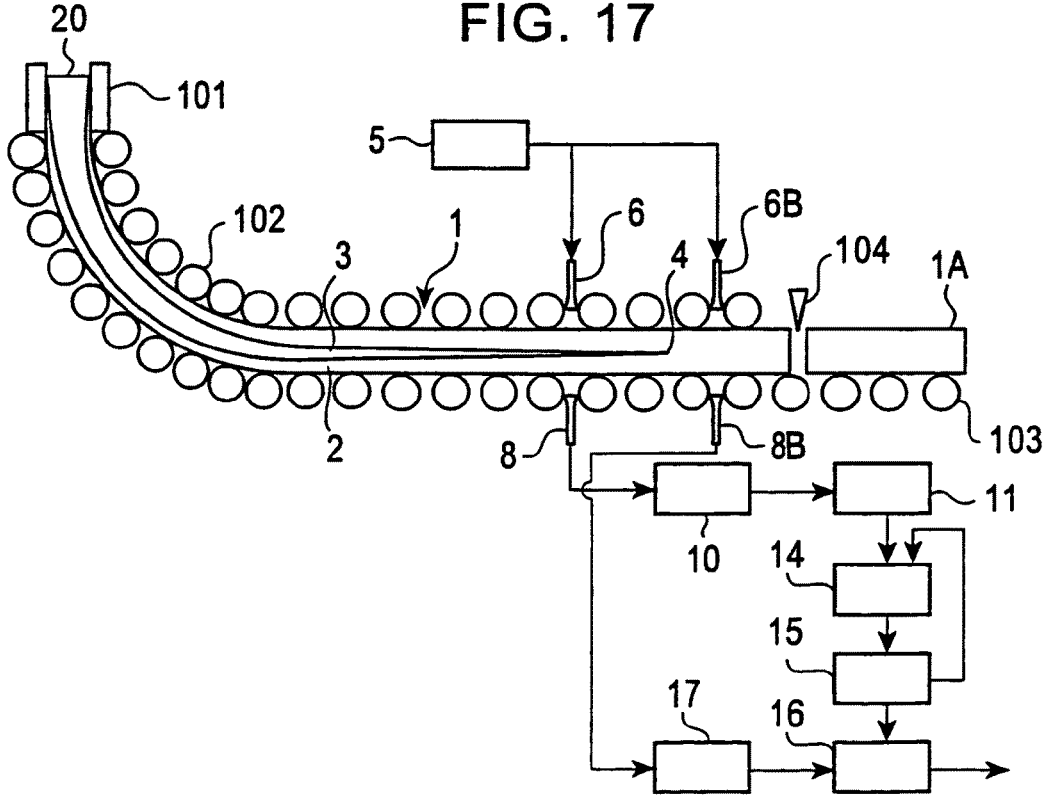
FIG. 17 shows a sixth embodiment of the present invention.
Reference numerals used in FIGS. 1 to 17 denote respective components as follows:
1 cast product (slab), 2 solid phase, 3 liquid phase, 4 crater end, 5 ultrasonic transmitting unit, 6 ultrasonic shear wave transmitter, 7 ultrasonic longitudinal wave transmitter, 8 ultrasonic shear wave receiver, 9 ultrasonic longitudinal wave receiver, 10 passed shear-wave intensity detecting unit, 11 crater end arrival detecting unit, 12 longitudinal-wave propagation time detecting unit, 13 crater end computing unit, 14 physical property value storage unit, 15 heat condition equation unit, 16 crater end estimating unit, 17 shear-wave propagation time detecting unit, 20 molten steel surface, 31 magnet, 32 longitudinal wave coil, 33 shear wave coil, 34 magnetic line of force, 35 eddy current, 36 eddy current, 37 ultrasonic longitudinal wave, 38 ultrasonic shear wave, 101 mold, 102 slab support roll, 103 conveying roll, and 104 slab cutting machine.

A sixth embodiment related to the method and apparatus for detecting the crater end from the casting conditions and the values of physical properties by calculation based on the heat condition equation will be described below. FIG. 17 shows a sixth embodiment of the present invention, and it is a schematic view of a slab continuous casting machine provided with a crater end detector according to the present invention.

As shown in FIG. 17, the crater end detector of the sixth embodiment comprises an ultrasonic shear wave sensor (hereinafter referred to as a "first ultrasonic shear wave sensor") made up of an ultrasonic shear wave transmitter 6 and an ultrasonic shear wave receiver 8 disposed in opposed relation with a slab 1 between them, a second ultrasonic shear wave sensor made up of an ultrasonic shear wave transmitter 6B and an ultrasonic shear wave receiver 8B disposed downstream of the first ultrasonic shear wave sensor in opposed relation with the slab 1 between them, an ultrasonic transmitting unit 5 which is an electric circuit for supplying an electric signal to each of the ultrasonic shear wave transmitter 6 and the ultrasonic shear wave transmitter 6B, thereby causing ultrasonic waves to be transmitted to the slab 1, a passed shear-wave intensity detecting unit 10 and a crater end arrival detecting unit 11 for processing a signal received by the ultrasonic shear wave receiver 8, a shear-wave propagation time detecting unit 17 for processing a signal received by the ultrasonic shear wave receiver 8B, a physical property value storage unit 14 for storing the values of physical properties used in the calculation based on the heat condition equation, a heat condition equation unit 15 for executing the calculation based on the heat condition equation, and a crater end estimating unit 16 for processing signals from the shear-wave propagation time detecting unit 17 and the heat condition equation unit 15.

The shear-wave propagation time detecting unit 17 detects the propagation time of the ultrasonic shear wave signal, which is passed through the slab 1, from the signal received by the ultrasonic shear wave receiver 8B, and it is constituted by a computer. The other components, i.e., the passed shear-wave intensity detecting unit 10, the crater end arrival detecting unit 11, the physical property value storage unit 14, the heat condition equation unit 15, and the crater end estimating unit 16 are the same as those in the fifth embodiment and have the same functions. A description of those components is omitted here.

A manner of processing the received signal will be described below. Manners of processing signals in the passed shear-wave intensity detecting unit 10, the crater end arrival detecting unit 11, the physical property value storage unit 14, and the heat condition equation unit 15 are the same as those in the fifth embodiment, and therefore a description of those manners is omitted here.

The operation of the shear-wave propagation time detecting unit 17 is basically the same as that of the longitudinal-wave propagation time detecting unit 12 in the fifth embodiment, and the shear-wave propagation time detecting unit 17 detects a time from the timing of transmitting the transmitted signal to the timing at which the ultrasonic shear wave passage signal appears. A method for detecting the ultrasonic shear wave passage signal can be practiced by detecting the timing at which the passage signal exceeds a threshold, or by detecting the timing at which the passage signal is maximized within a gate as shown in FIG. 3.

The crater end estimating unit 16 determines the relationship between the propagation time of the ultrasonic shear wave signal detected by the shear-wave propagation time detecting unit 17 and the crater end computed by the heat condition equation unit 15 in a similar manner to that in the fifth embodiment described above with reference to FIG. 16, for example, and then estimates the crater end 4 from the propagation time of the ultrasonic shear wave signal, which has been measured by the shear-wave propagation time detecting unit 17, based on the determined relationship. Thus, in the sixth embodiment, the crater end 4 is determined using the propagation time of the ultrasonic shear wave signal instead of the propagation time of the ultrasonic longitudinal wave signal used in the fifth embodiment. Accordingly, the calibration of the physical property value used in the calculation based on the heat condition equation, etc. are performed as in the fifth embodiment.

While the second ultrasonic shear wave sensor is installed in the sixth embodiment to measure the propagation time of the ultrasonic shear wave signal, the installation of the second ultrasonic shear wave sensor is not always required, and the first ultrasonic shear wave sensor made up of the ultrasonic shear wave transmitter 6 and the ultrasonic shear wave receiver 8 can also be used as the ultrasonic shear wave sensor for measuring the propagation time. In the case of determining the crater end 4 from the propagation time of the ultrasonic shear wave signal, however, the crater end can be determined in a restricted range, i.e., only when the crater end 4 is positioned upstream of the installed position of the ultrasonic shear wave sensor. Therefore, care has been taken for the installed position of the sensor.

By employing the crater end detecting methods and apparatuses according to the first to sixth embodiments described above, the crater end 4 can be precisely confirmed online and can be controlled with adjustment of operation parameters. As a result, productivity can be increased by positioning the crater end 4 as close as possible to the end of the continuous casting machine, or central segregation can be reduced by always holding the crater end within the soft reduction zone.

The operation parameters adaptable for control of the crater end 4 include, for example, the casting speed, the amount of secondary cooling water (increase/decrease of the overall amount, a water amount distribution pattern in the lengthwise direction, and a water amount distribution pattern in the transverse direction), a roll gap pattern, change in power of electromagnetic stirring, change of mold powder (brand), the degree of superheat of molten steel (control using a heat-insulating cover or heating powder). By experimentally or theoretically confirming the relationship between those casting conditions and the crater end 4 in advance, the crater end 4 can be precisely controlled with adjustment of the operation parameters.

The present invention is not limited to the above-described matters and can be variously modified without departing from the scope of the present invention. For example, while the above description is made as using the electromagnetic ultrasonic sensor, the ultrasonic longitudinal wave can also be transmitted and received by a method of contacting a piezoelectric oscillator with water, or a laser ultrasonic method. A method of transmitting the ultrasonic longitudinal wave by the laser ultrasonic method and receiving it by the electromagnetic ultrasonic method is also useful in point of increasing measurement sensitivity.

Further, while in the above-described embodiments a pair of the ultrasonic shear wave transmitter 6 and the ultrasonic shear wave receiver 8 and/or a pair of the ultrasonic longitudinal wave transmitter 7 and the ultrasonic longitudinal wave receiver 9 are installed with the slab 1 located therebetween to perform measurement by a passage method, the transmitter and the receiver may be disposed on one surface of the slab 1 to perform measurement by a reflection method using an echo reflected by the other opposite surface of the slab 1. The term "ultrasonic sensor" used in the present invention includes any of those types of sensors. Also, in the present invention, the calibration of the calculation formula for computing the crater end from the propagation time, the calibration of the physical property value used in the calculation based on the heat condition equation, and/or the preparation of the approximation formula or the table representing the relationship between the propagation time and the crater end may be performed at a plurality of optional positions in the transverse direction of the slab. By setting a plurality of optional positions in the transverse direction of the slab and employing a different calculation formula for each position, it is possible to reduce influences of unevenness of cooling and fluctuations of thickness in the transverse direction of the slab, and to increase the measurement accuracy at each position. In that case, when a plurality of ultrasonic sensors are disposed in the upstream and downstream sides, those ultrasonic sensors are required to perform the measurements at the same positions in the transverse direction with respect to the slab 1.

Moreover, in the above-described embodiments, the crater end 4 is estimated in the continuous casting machine for which are performed the calibration of the calculation formula for computing the crater end from the propagation time, the calibration of the physical property value used in the calculation based on the heat condition equation, and/or the preparation of the approximation formula or the table representing the relationship between the propagation time and the crater end. However, the calibrated calculation formula, the calibrated physical property value, and/or the approximation formula or the table representing the relationship between the propagation time and the crater end can also be employed to estimate the crater end in another continuous casting machine. In that case, the ultrasonic longitudinal wave sensor is also required to be disposed in the other continuous casting machine in order to confirm the propagation time of the ultrasonic longitudinal wave signal, for example. In not only another continuous casting machine, but also the same continuous casting machine, the calibrated calculation formula, the calibrated physical property value, and/or the approximation formula or the table representing the relationship between the propagation time and the crater end can also be inputted and used for a new ultrasonic sensor exchanged due to a failure, renewal or other reason.

While the first to third embodiments have been described in connection with the case of directly computing the crater end 4 from the propagation time of the ultrasonic longitudinal wave signal by using a linear equation, a polynomial, such as an equation of the second or third degree, can also be used. Alternatively, the crater end may be determined through the steps of obtaining the thickness of the solid phase 2 from the propagation time of the ultrasonic longitudinal wave signal and computing the crater end from the obtained thickness of the solid phase 2 and the casting speed. In that case, the calibration may be performed such that, at the timing at which the passage of the crater end is determined using the ultrasonic shear wave, the solid phase thickness (d) obtained based on the above-described formula (1) becomes ½ of the slab thickness (D).

Regarding the electromagnetic ultrasonic sensor for generating and detecting the ultrasonic longitudinal wave and the ultrasonic shear wave at the same position, the longitudinal wave coil and the shear wave coil can be constituted as the same coil, instead of separately arranging the longitudinal wave coil and the shear wave coil from each other, by alternately changing the polarity of each magnetic pole of the sensor.

The operator may perform the determination to be made in the crater end arrival detecting unit 11 and may instruct the timing of the determination as to the passage of the crater end to the crater end computing unit 13. Moreover, after collecting data, the determination as to the passage of the crater end, the calibration, and the estimation of the crater end may be manually performed on a desk.

Still further, in the fourth to sixth embodiments, the heat condition equation is calibrated through the steps of changing the casting speed in several stages and obtaining the casting speed at which the crater end is matched with the position of the ultrasonic shear wave sensor in the stationary region. However, the heat condition equation can also be calibrated by measuring the timing at which the crater end passes the position of the ultrasonic shear wave sensor in a non-stationary region and by using a heat condition equation in consideration of the non-stationary region as well.

INDUSTRIAL APPLICABILITY

According to the present invention, at the time when the crater end of the slab is detected by the ultrasonic shear wave sensor, the crater end determined from the propagation time of the ultrasonic longitudinal wave signal measured by the ultrasonic longitudinal wave sensor or the crater end determined by the calculation based on the heat condition equation is calibrated. Therefore, the crater end of the slab can be accurately detected only from the measured values of the ultrasonic shear wave sensor and/or the ultrasonic longitudinal wave sensor without performing troublesome calibration operation such as driving rivets into the slab. As a result, it is possible to confirm the crater end during the casting with high accuracy under various casting conditions for all varieties of chemical components, to increase productivity by utilizing the length of the continuous casting machine up to a maximum limit, and to produce the slab with reduced central segregation by properly applying soft reduction. Hence, the present invention can provide an industrially valuable advantage.

What is claimed is:

1. A method for detecting a crater end of a continuously cast product, the method comprising the steps of
    installing an ultrasonic shear wave sensor for transmitting an ultrasonic shear wave to the continuously cast product and receiving the transmitted ultrasonic shear wave in a continuous casting machine,
    detecting based on variations of an ultrasonic signal received by the ultrasonic shear wave sensor that the crater end of the cast product is matched with the installed position of the ultrasonic shear wave sensor,
    calibrating a physical property value of the cast product used in a calculation based on a heat condition equation in solidifying the cast product, the physical property value being at least one of density, enthalpy, thermal conductivity, solidus temperature, heat removed in the mold, heat transfer coefficient in a secondary cooling zone, and temperature of molten steel, such that the crater end computed based on the heat condition equation using casting conditions at that time is matched with the installed position of the ultrasonic shear wave sensor, and after the calibration, determining the crater end by the calculation based on the heat condition equation under respective casting conditions by using the calibrated physical property value.

2. A method for detecting a crater end of a continuously cast product, the method comprising the steps of executing the calculation based on the heat condition equation by using the physical property value calibrated by the method according to claim 1 and the casting conditions of a different continuous casting machine, and determining the crater end in the different continuous casting machine.

3. A method for detecting a crater end of a continuously cast product, the method comprising the steps of determining the crater end of the cast product by the method for detecting a crater end of a continuously cast product according to claim 1, and adjusting a casting speed or intensity of secondary cooling for the cast product in accordance with the result of the step of determining the crater.

4. A method for detecting a crater end of a continuously cast product, the method comprising the steps of installing an ultrasonic shear wave sensor for transmitting an ultrasonic shear wave to the continuously cast product and receiving the transmitted ultrasonic shear wave in a continuous casting machine, detecting based on variations of an ultrasonic signal received by the ultrasonic shear wave sensor that the crater end of the cast product is matched with the installed position of the ultrasonic shear wave sensor, calibrating a physical property value of the cast product used in a calculation based on a heat condition equation in solidifying the cast product, the physical property value being at least one of density, enthalpy, thermal conductivity, solidus temperature, heat removed in the mold, heat transfer coefficient in a secondary cooling zone, and temperature of molten steel, such that the crater end computed based on the heat condition equation using casting conditions at that time is matched with the installed position of the ultrasonic shear wave sensor, determining the crater ends by the calculation based on the heat condition equation by using the calibrated physical property value and measuring propagation times by the ultrasonic shear wave sensor under various casting conditions, obtaining a relationship between crater ends computed based on the heat condition equation and the propagation times measured by the ultrasonic shear wave sensor, and determining the crater end from the propagation time measured by the ultrasonic shear wave sensor based on the obtained relationship.

5. A method for detecting a crater end of a continuously cast product, the method comprising the step of, based on the relationship between the crater ends computed based on the heat condition equation and the propagation times measured by the ultrasonic sensor in the continuous casting machine, which is obtained by the method according to claim 4, determining the crater end in a different continuous casting machine from a propagation time of an ultrasonic signal measured by an ultrasonic shear wave sensor or an ultrasonic longitudinal wave sensor installed in the different continuous casting machine.

6. A method for detecting a crater end of a continuously cast product, the method comprising the steps of determining the crater end of the cast product by the method for detecting a crater end of a continuously cast product according to claim 4, and adjusting a casting speed or intensity of secondary cooling for the cast product in accordance with the result of the step of determining the crater end.

7. A method for detecting a crater end of a continuously cast product, the method comprising the steps of installing, in a continuous casting machine, a first ultrasonic shear wave sensor for transmitting an ultrasonic shear wave to the continuously cast product and receiving the transmitted ultrasonic shear wave and at least one of an ultrasonic longitudinal wave sensor for transmitting an ultrasonic longitudinal wave to the continuously cast product and receiving the transmitted ultrasonic longitudinal wave and a second ultrasonic shear wave sensor for transmitting an ultrasonic shear wave and receiving the transmitted ultrasonic shear wave, detecting based on variations of an ultrasonic signal received by the first ultrasonic shear wave sensor that the crater end of the cast product is matched with the installed position of the first ultrasonic shear wave sensor, calibrating a physical property value of the cast product used in a calculation based on a heat condition equation in solidifying the cast product, the physical property value being at least one of density, enthalpy, thermal conductivity, solidus temperature, heat removed in the mold, heat transfer coefficient in a secondary cooling zone, and temperature of molten steel, such that the crater end computed based on the heat condition equation using casting conditions at that time is matched with the installed position of the first ultrasonic shear wave sensor, determining crater ends by the calculation based on the heat condition equation by using the calibrated physical property value and measuring propagation times by the ultrasonic longitudinal wave sensor or the second ultrasonic shear wave sensor under various casting conditions, obtaining a relationship between the crater ends computed based on the heat condition equation and the propagation times measured by the ultrasonic longitudinal wave sensor or the second ultrasonic shear wave sensor, and determining the crater end from the propagation time measured by the ultrasonic longitudinal wave sensor or the second ultrasonic shear wave sensor based on the obtained relationship.

8. A method for detecting a crater end of a continuously cast product, the method comprising the step of, based on the relationship between the crater ends computed based on the heat condition equation and the propagation times measured by the ultrasonic sensor in the continuous casting machine, which is obtained by the method according to claim 7, determining the crater end in a different continuous casting machine from a propagation time of an ultrasonic signal measured by an ultrasonic shear wave sensor or an ultrasonic longitudinal wave sensor installed in the different continuous casting machine.

9. A method for detecting a crater end of a continuously cast product, the method comprising the steps of determining the crater end of the cast product by the method for detecting a crater end of a continuously cast product according to claim 7, and adjusting a casting speed or intensity of secondary cooling for the cast product in accordance with the result of the step of determining the crater end.

10. An apparatus for detecting a crater end of a continuously cast product, the apparatus comprising
an ultrasonic shear wave sensor made up of an ultrasonic shear wave transmitter for transmitting an ultrasonic shear wave to the continuously cast product and an ultrasonic shear wave receiver for receiving the transmitted ultrasonic shear wave, and
a heat condition equation unit constituted by a computer, for executing calculations based on a heat condition equation in solidifying the cast product in accordance with casting conditions and values of physical properties of the cast product, wherein the values of physical properties includes at least one of density, enthalpy, thermal conductivity, solidus temperature, heat removed in the mold, heat transfer coefficient in a secondary cooling zone, and the temperature of molten steel, thereby determining the crater end of the cast product,
wherein at the time when it is confirmed based on variations of an ultrasonic signal received by the ultrasonic shear wave sensor that the installed position of the ultrasonic shear wave sensor and the crater end of the cast product are matched with each other, the heat condition equation unit calibrates at least one of the values of physical properties used in the calculation based on the heat condition equation such that the crater end computed by the heat condition equation unit is matched with the installed position of the ultrasonic shear wave sensor.

11. An apparatus for detecting a crater end of a continuously cast product, the apparatus comprising
an ultrasonic shear wave sensor made up of an ultrasonic shear wave transmitter for transmitting an ultrasonic shear wave to the continuously cast product and an ultrasonic shear wave receiver for receiving the transmitted ultrasonic shear wave,
a heat condition equation unit constituted by a computer for executing calculations based on a heat condition equation in solidifying the cast product in accordance with casting conditions and values of physical properties of the cast product, wherein the values of physical properties includes at least one of density, enthalpy, thermal conductivity, solidus temperature, heat removed in the mold, heat transfer coefficient in a secondary cooling zone, and temperature of molten steel, thereby determining the crater end of the cast product, and
a crater end estimating unit for estimating the crater end of the cast product based on a relationship between an ultrasonic signal received by the ultrasonic shear wave sensor and the crater end computed by the heat condition equation unit,
wherein at the time when it is confirmed based on variations of the ultrasonic signal received by the ultrasonic shear wave sensor that the installed position of the ultrasonic shear wave sensor and the crater end of the cast product are matched with each other, the heat condition equation unit calibrates at least one of the values of physical properties used in the calculation based on the heat condition equation such that the crater end computed by the heat condition equation unit is matched with the installed position of the ultrasonic shear wave sensor,
wherein after the calibration of the physical property value, the crater end estimating unit obtains a relationship between the ultrasonic signal received by the ultrasonic shear wave sensor and the crater end computed by the heat condition equation unit, and wherein the crater end is determined from a propagation time measured by the ultrasonic shear wave sensor based on the obtained relationship.

12. An apparatus for detecting a crater end of a continuously cast product, the apparatus comprising
an ultrasonic shear wave sensor made up of an ultrasonic shear wave transmitter for transmitting an ultrasonic shear wave to the continuously cast product and an ultrasonic shear wave receiver for receiving the transmitted ultrasonic shear wave,
an ultrasonic longitudinal wave sensor made up of an ultrasonic longitudinal wave transmitter for transmitting an ultrasonic longitudinal wave to the continuously cast product and an ultrasonic longitudinal wave receiver for receiving the transmitted ultrasonic longitudinal wave,
a heat condition equation unit constituted by a computer, for executing calculations based on a heat condition equation in solidifying the cast product in accordance with casting conditions and values of physical properties of the cast product, wherein the values of physical properties includes at least one of density, enthalpy, thermal conductivity, solidus temperature, heat removed in the mold, heat transfer coefficient in a second cooling zone, and temperature of molten steel, thereby determining the crater end of the cast product, and a crater end estimating unit for estimating the crater end of the cast product based on a relationship between an ultrasonic signal received by the ultrasonic shear wave sensor and the crater end computed by the heat condition equation unit, wherein at the time when it is confirmed based on variations of the ultrasonic signal received by the ultrasonic shear wave sensor that the installed position of the ultrasonic shear wave sensor and the crater end of the cast product are matched with each other, the heat condition equation unit calibrates at least one of the values of physical properties used in the calculation based on the heat condition equation such that the crater end computed by the heat condition equation unit is matched with the installed position of the ultrasonic shear wave sensor,
wherein after the calibration of the physical property value, the crater end estimating unit obtains a relationship between an ultrasonic signal received by the ultrasonic longitudinal wave sensor and the crater end computed by the heat condition equation unit, and
wherein the crater end is determined from a propagation time measured by the ultrasonic longitudinal wave sensor based on the obtained relationship.

13. The apparatus according to any one of claims 10 to 12, further comprising a physical property value storage unit for storing the values of physical properties of the cast product and for providing the values to the heat condition equation unit,
wherein, after the calibration of the physical property value, the calibrated value is inputted from the heat condition equation unit to the physical property value storage unit.

* * * * *